(12) United States Patent
Ray, II

(10) Patent No.: US 10,813,897 B2
(45) Date of Patent: *Oct. 27, 2020

(54) COMPOSITION AND METHOD FOR COMPOUNDED THERAPY

(71) Applicant: CMPD LICENSING, LLC, Conroe, TX (US)

(72) Inventor: Jay Richard Ray, II, Conroe, TX (US)

(73) Assignee: CMPD Licensing, LLC, Conroe, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/996,560

(22) Filed: Jan. 15, 2016

(65) Prior Publication Data
US 2016/0128959 A1 May 12, 2016

Related U.S. Application Data

(63) Continuation-in-part of application No. 13/448,088, filed on Apr. 16, 2012, now Pat. No. 9,468,599, which is a continuation of application No. 13/409,738, filed on Mar. 1, 2012, now abandoned, which is a continuation-in-part of application No. 13/337,598, filed on Dec. 27, 2011, now abandoned.

(51) Int. Cl.
A61K 31/196 (2006.01)
A61K 9/06 (2006.01)
A61K 31/167 (2006.01)
A61K 9/00 (2006.01)
A61K 31/195 (2006.01)
A61K 31/53 (2006.01)
A61K 31/7048 (2006.01)
A61K 31/5415 (2006.01)

(52) U.S. Cl.
CPC .......... A61K 31/196 (2013.01); A61K 9/0014 (2013.01); A61K 9/06 (2013.01); A61K 31/167 (2013.01); A61K 31/195 (2013.01); A61K 31/53 (2013.01); A61K 31/5415 (2013.01); A61K 31/7048 (2013.01)

(58) Field of Classification Search
CPC ...... A61K 9/06; A61K 31/167; A61K 31/195; A61K 31/196
See application file for complete search history.

(56) References Cited

U.S. PATENT DOCUMENTS

| 3,711,602 A | 1/1973 | Herschler |
| 4,562,060 A | 12/1985 | Broberg et al. |
| 4,937,078 A | 6/1990 | Mezei et al. |
| 5,374,661 A * | 12/1994 | Betlach, II ........... A61K 9/0014 514/772.4 |
| 5,993,836 A | 11/1999 | Castillo |
| 6,248,789 B1 | 6/2001 | Weg |
| 6,290,986 B1 * | 9/2001 | Murdock ............... A61F 13/00 424/447 |
| 6,299,902 B1 | 10/2001 | Jun et al. |
| 6,410,062 B1 | 6/2002 | Callaghan et al. |
| 7,166,641 B2 | 1/2007 | Lee et al. |
| 7,691,404 B2 * | 4/2010 | Song ..................... A61K 9/7053 424/443 |
| 8,535,738 B2 | 9/2013 | Collins et al. |
| 2001/0029257 A1 | 10/2001 | Murdock et al. |
| 2003/0124176 A1 | 7/2003 | Hsu et al. |
| 2004/0068007 A1 * | 4/2004 | Lee ...................... A61K 31/167 514/554 |
| 2004/0101582 A1 | 5/2004 | Wolicki |
| 2004/0208914 A1 * | 10/2004 | Richlin ................ A61K 9/0014 424/448 |
| 2004/0265364 A1 | 12/2004 | Ozturk et al. |
| 2005/0038062 A1 | 2/2005 | Burns et al. |
| 2005/0187212 A1 | 8/2005 | Ohki et al. |
| 2006/0140986 A1 | 6/2006 | Fita |
| 2006/0223788 A1 | 10/2006 | Cathcart |
| 2007/0065463 A1 | 3/2007 | Aung-Din |
| 2007/0093420 A1 | 4/2007 | Yeomans et al. |
| 2007/0116730 A1 | 5/2007 | Simmons et al. |
| 2007/0269393 A1 | 11/2007 | Wepfer |
| 2007/0269465 A9 | 11/2007 | Fita |
| 2008/0233183 A1 | 9/2008 | McCook et al. |
| 2009/0162421 A1 | 6/2009 | Geisslinger et al. |
| 2010/0016436 A1 | 1/2010 | Staniforth et al. |
| 2010/0080797 A1 | 4/2010 | Yeomans et al. |
| 2010/0160299 A1 | 6/2010 | Baker et al. |
| 2010/0184817 A1 | 7/2010 | Wolicki |
| 2010/0221309 A1 | 9/2010 | Myers et al. |
| 2010/0226972 A1 | 9/2010 | Lutz |
| 2010/0286205 A1 | 11/2010 | McCarron et al. |
| 2010/0287884 A1 | 11/2010 | Seshadri et al. |

(Continued)

FOREIGN PATENT DOCUMENTS

EP 0964552 8/2009
IN 373/MUM/2005 3/2007

(Continued)

OTHER PUBLICATIONS

Pain Management Compounding. pp. 1-6, Published online 2010.*

(Continued)

Primary Examiner — Theodore R. West
Assistant Examiner — George W Kosturko
(74) Attorney, Agent, or Firm — Akerman LLP

(57) ABSTRACT

A method of producing a compounded medication may include formulating a compounded transdermal cream that includes combining a diclofenac sodium solution and a lidocaine and prilocaine cream. The diclofenac sodium solution may be combined in an amount providing a diclofenac concentration of between approximately 0.1% and approximately 0.75% by weight of the compounded transdermal cream. The lidocaine and prilocaine cream may be combined in an amount providing an approximate equivalent concentration of each of lidocaine and prilocaine between approximately 1.5% and approximately 2.25% by weight of the compounded transdermal cream.

8 Claims, 2 Drawing Sheets

(56) References Cited

U.S. PATENT DOCUMENTS

| | | | |
|---|---|---|---|
| 2011/0015229 | A1 | 1/2011 | Zhang et al. |
| 2011/0028460 | A1 | 2/2011 | Kisak et al. |
| 2011/0033545 | A1 | 2/2011 | Wang |
| 2011/0250212 | A1 | 10/2011 | Yeomans et al. |
| 2011/0257257 | A1 | 10/2011 | Shapira et al. |
| 2011/0294763 | A1* | 12/2011 | Dordunoo ............ A61K 9/0014 514/161 |
| 2013/0085171 | A1 | 4/2013 | Ray |
| 2013/0165429 | A1 | 6/2013 | Ray et al. |
| 2013/0165430 | A1 | 6/2013 | Ray et al. |
| 2015/0148305 | A1 | 5/2015 | Ray et al. |
| 2015/0297507 | A1* | 10/2015 | Grenier ................ A61P 17/02 424/450 |
| 2015/0359740 | A1 | 12/2015 | Ray |
| 2015/0359767 | A1 | 12/2015 | Ray |
| 2015/0359768 | A1 | 12/2015 | Ray |

FOREIGN PATENT DOCUMENTS

| | | | |
|---|---|---|---|
| JP | 7309749 | 11/1995 | |
| WO | WO 2004/110423 | 12/2004 | |
| WO | WO 2008049020 A2 * | 4/2008 | ........... A61K 9/0014 |
| WO | WO-2008049020 A2 * | 4/2008 | ........... A61K 9/0014 |
| WO | WO 2013/048453 | 4/2013 | |
| WO | WO 2013/101949 | 7/2013 | |

OTHER PUBLICATIONS

Akorn et al., (EMLA Cream Product Page). Pages 1-4. Published 2008.*

Lee et al., Cosmetic Dermatology vol. 16 pp. 31-35. Published 2003.*

Pain Management Compounding (Published online 2010).*

Akorn Pharmaceuticals (EMLA Cream product page, published 2007).*

Kumar et al (Journal of Endourology vol. 21, pp. 578-586, published 2007).*

Pain Management Compounding (Published online 2010) (Year: 2010).*

Akorn Pharmaceuticals (EMLA Cream product page, published 2007), (Year: 2007).*

Lee et al (Cosmetic Dermatology vol. 16 pp. 35-38, published 2003) (Year: 2003).*

U.S. Appl. No. 13/409,738, filed Mar. 1, 2012, Ray et al.

U.S. Appl. No. 13/337,598, filed Dec. 27, 2011, Ray et al.

U.S. Appl. No. 61/541,716, filed Sep. 30, 2011, Ray.

Airaksinen O, et al. (1993) Ketoprofen 2.5% gel versus placebo gel in the treatment of acute soft tissue injuries. Int J Clin Pharmacol Ther Toxicol. 31(11):561-563. (Abstract Only).

Akarsu S, et al. (2011) Comparison of topical 3% diclofenac sodium gel and 5% imiquimod cream for the treatment of actinic keratoses. Clin Exp Dermatol. 36(5):479-484.

Akbay BK, et al. (2010). Analgesic efficacy of topical tramadol in the control of postoperative pain in children after tonsillectomy. J Anesth. 24(5):705-708.

Akermark C, et al. (1990) Topical indomethacin in overuse injuries in athletes. A randomized double-blind study comparing Elmetacin with oral indomethacin and placebo. Int J Sports Med. 11(5):393-396.

Akinturk S, et al (2007) Effect of piroxicam gel for pain control and inflammation in Nd:YAG 1064-nm laser hair removal. J Eur Acad Dermatol Venereol. 21(3):380-383. (Abstract Only).

Akinturk S, et al. (2009) A clinical comparison of topical piroxicam and Emla cream for pain relief and inflammation in laser hair removal. Lasers Med Sci. 24(4):535-538.

Alañón F, et al. (2014) Comparison between topical anaesthesia with cocaine versus lidocaine plus adrenaline for outpatient laser dacryocystorhinostomy. Arch Soc Esp Oftalmol. 89(2):53-57.

Allegrini A, et al. (2009) Efficacy and safety of piroxicam patch versus piroxicam cream in patients with lumbar osteoarthritis. A randomized, placebo-controlled study. Arzneimittelforschung. 59(8):403-409.

Alsarra IA. (2008) Evaluation of proniosomes as an alternative strategy to optimize piroxicam transdermal delivery. J Microencapsul. 26(3):272-278.

Altman R, et al. (2009) Topical therapy for osteoarthritis: clinical and pharmacologic perspectives. Postgrad Med. 121(2):139-147. (Abstract Only).

Ambade KW, et al. (2008) Formulation and evaluation of flurbiprofen microemulsion. Curr Drug Deliv. 5(1):32-41.

Ambler JJ, et al. (2005) The effect of topical non-steroidal anti-inflammatory cream on the incidence and severity of cutaneous burns following external DC cardioversion. Resuscitation. 65(2):173-178.

Arapoglou V, et al. (2011) Analgesic efficacy of an ibuprofen-releasing foam dressing compared with local best practice for painful exuding wounds. J Wound Care. 20(7):319-320, 322-325.

Argoff CE. (2004) Topical treatments for pain. Curr Pain Headache Rep. 8(4):261-267. (Abstract Only).

Arnau B, et al. (2013) Lidocaine-prilocaine (EMLA(®)) cream as analgesia in hysteroscopy practice: a prospective, randomized, non-blinded, controlled study. Acta Obstet Gynecol Scand. 92(8):978-981.

Ashfield T. (2005) The use of topical opioids to relieve pressure ulcer pain. Nurs Stand. 19(45):90-92. (Abstract Only).

Assouline M, et al. (1998) A prospective randomized trial of topical soluble 0.1% indomethacin versus 0.1% diclofenac versus placebo for the control of pain following excimer laser photorefractive keratectomy. Ophthalmic Surg Lasers. 29(5):365-374.

Attia MA, et al. (2004) Transbuccal permeation, anti-inflammatory activity and clinical efficacy of piroxicam formulated in different gels. Int J Pharm. 276(1-2): 11-28.

Audeval-Gerard C, et al. (2000) Pharmacokinetics of ketoprofen in rabbit after a single topical application. Eur J Drug Metab Pharmacokinet. 25(34):227-230. (Abstract Only).

Azevedo VM, et al. (2000) Transdermal ketamine as an adjuvant for postoperative analgesia after abdominal gynecological surgery using lidocaine epidural blockade. Anesth Analg. 91(6):1479-1482.

B&B Compounding Pharmacy. (2010) Pain Management Compounding. Available at http://www.bbpharmacy.com/paincompounding.html. (5 pages).

Badalà F, et al. (2004) Effect of topical 0.1% indomethacin solution versus 0.1% fluorometholon acetate on ocular surface and pain control following laser subepithelial keratomileusis (LASEK). Cornea. 23(6):550-553.

Baixauli F, et al. (1990) Percutaneous treatment of acute soft tissue lesions with naproxen gel and ketoprofen gel. J Int Med Res. 18(5):372-378. (Abstract Only).

Barthel HR, et al. (2009) Randomized controlled trial of diclofenac sodium gel in knee osteoarthritis. Semin Arthritis Rheum. 39(3):203-212.

Barton DL, et al. (2011) A double-blind, placebo-controlled trial of a topical treatment for chemotherapy-induced peripheral neuropathy: NCCTG trial N06CA. Support Care Cancer. 19(6):833-841.

Bernstein JE, et al. (1981) Inhibition of histamine-induced pruritus by topical tricyclic antidepressants. J Am Acad Dermatol. 5(5):582-585.

Bhaskar K, et al. (2009) Lipid nanoparticles for transdermal delivery of flurbiprofen: formulation, in vitro, ex vivo and in vivo studies. Lipids Health Dis. 8:6.

Boardman LA, et al. (2008) Topical gabapentin in the treatment of localized and generalized vulvodynia. Obstet Gynecol. 112(3):579-585.

Bourolias C, et al. (2010) Lidocaine spray vs tetracaine solution for transnasal fiber-optic laryngoscopy. Am J Otolaryngol. 31(2):114-116.

Campbell J, et al. (1994) Evaluation of topical ibuprofen cream in the treatment of acute ankle sprains. J Acid Emerg Med. 11(3):178-182.

(56) References Cited

OTHER PUBLICATIONS

Campione E, et al. (2010) Topical treatment of actinic keratoses with piroxicam 1% gel: a preliminary open-label study utilizing a new clinical score. Am J Clin Dermatol. 11(1):45-50.
Canbay O, et al. (2008) Topical ketamine and morphine for post-tonsillectomy pain. Eur J Anaesthesiol. 25(4):287-292. (Abstract Only).
Christensen TJ, et al. (2013) Lidocaine analgesia for removal of wound vacuum-assisted closure dressings: a randomized double-blinded placebo-controlled trial. J Orthop Trauma. 27(2):107-112.
Cigna E, et al. (2009) Evaluation of polyurethane dressing with ibuprofen in the management of split-thickness skin graft donor sites. In Vivo. 23(6):983-936.
Conaghan PG, et al. (2013) A multicentre, randomized, placebo- and active-controlled trial comparing the efficacy and safety of topical ketoprofen in Transfersome gel (IDEA-033) with ketoprofen-free vehicle (TDT 064) and oral celecoxib for knee pain associated with osteoarthritis. Rheumatology (Oxford). 52(7):1303-1312.
Cordero JA, et al. (2001) In vitro based index of topical anti-inflammatory activity to compare a series of NSAIDs. Eur J Pharm Biopharm. 51(2):135-42. (Abstract Only).
Coudert AE, et al. (2014) Phase III, randomized, double-blind, placebo-controlled trial of topical 2 % lidocaine for the prevention and treatment of oral mucosal pain in children. Clin Oral Investig. 18(4):1189-1194.
Crowley KL, et al. (1998) Clinical application of ketamine ointment in the treatment of sympathetically maintained pain. Int J Pharm Compd. 2(2): 122-127.
Dinsmore WW, et al. (2007) Topical eutectic mixture for premature ejaculation (TEMPE): a novel aerosol-delivery form of lidocaine-prilocaine for treating premature ejaculation. BJU Int. 99(2):369-375.
Dissanayake VU, et al. (1997) Spermine modulation of specific [3H]-gabapentin binding to the detergent-solubilized porcine cerebral cortex alpha 2 delta calcium channel subunit. Br J Pharmacol. 120(5):833-840.
Doliwa A, et al. (2001) Transdermal Iontophoresis and skin retention of piroxicam from gels containing piroxicam: hydroxypropyl-beta-cyclodextrin complexes. Drug Dev Ind Pharm. 27(8):751-758.
Dreiser RL, et al. (1994) Flurbiprofen local action transcutaneous (LAT): clinical evaluation in the treatment of acute ankle sprains. Eur J Rheumatol Inflamm. 14(4):9-13.
Dutta A, et al. (2003) Piroxicam gel, compared to EMLA cream is associated with less pain after venous cannulation in volunteers. Can J Anaesth. 50(8):775-778.
El Gendy AM, et al. (2002) in vitro release studies of flurbiprofen from different topical formulations. Drug Dev Ind Pharm. 28(7):823-831.
Erickson MA. (2005) Can you provide a formulation for compounding meloxicam oral suspension? Pharmacy Times—Compoundingh-Hotline. Available at http://www.pharmacytimes.com/publications/issue/2005/2005-01/2005-01-9197.
Esparza F, et al. (2006) Topical ketoprofen TDS patch versus diclofenac gel: efficacy and tolerability in benign sport related soft-tissue injuries. Br J Sports Med. 41(3):134-139.
Federal Drug Agency. (1996) TOPAMAX—Highlights of Prescribing Information. (27 pages).
Federal Drug Agency. (2010) MOBIC—Highlights of Prescribing Information. (15 pages).
Fibromyalgia General Discussion—"So Many Questions—Please Read and Advise" (Jan. 15, 2011), available at http://www.fibromyalgia-symptoms.org/forums/fibromyalgia_general_discussion/so_many_questions_please_read_and_advise/.
Fraczek M, et al. (2012) Assessment of the efficacy of topical anesthetics using the tactile spatial resolution method. Acta Dermatovenerol Croat. 20(1):7-13.
Franchi M, et al. (2009) Comparison between lidocaine-prilocaine cream (EMLA) and mepivacaine infiltration for pain relief during perineal repair after childbirth: a randomized trial. Am J Obstet Gynecol. 201(2):186.e1-5.

Franz TJ, et al. (1990) The use of water permeability as a means of validation for skin integrity in in vitro percutaneous-absorption studies. J Invest Dermatol. 94(4):525. (Abstract Only).
Franz TJ, et al. (2008) The cadaver skin absorption mode and the drug development process. Pharmacopeial Forum. 34(5).
Franz TJ, et al. (2009) Use of excised human skin to assess the bioequivalence of topical products. Skin Pharmacol Physiol. 22(5):276-286.
Franz TJ. (1975) Percutaneous absorption on the relevance of in vitro data. J Invest Dermatol. 64(3):190-195.
Funosas ER, et al. (2009) The use of topical subgingival gels of non-steroidal anti-inflammatory drugs (NSAIDs) as an adjunct to non-surgical management of chronic periodontitis. Acta Odontol Latinoam. 22(3):215-219.
Gammaitoni A, et al. (2007) Topical ketamine gel: possible role in treating neuropathic pain. Pain Med. 1(1):97-100.
Gaviola GC, et al. (2013) A prospective, randomized, double-blind study comparing the efficacy of topical anesthetics in nasal endoscopy. Laryngoscope. 123(4):852-858.
Gencer ZK, et al. (2013) Comparison of ropivacaine, bupivacaine, prilocaine, and lidocaine in the management of pain and hemorrhage during nasal pack removal. Am J Rhinol Allergy. 27(5):423-425.
Gennaro AR. (Editor) (1995) Remington: Practice of the Science and Pharmacy (19th Edition) (Philadelphia, PA: Lippincott Williams & Wilkins)—Chapter 66(pp. 1516-1517).
Gerbino PR. (1995) Remington: Practice of the Science and Pharmacy (21st Edition) (Philadelphia, PA: Lippincott Williams & Wilkins)—Chapter 39 (pp. 745-747, 759-760, 768-770), Chapter 44 (871-877).
Gerner P, et al. (2003) Topical amitriptyline in healthy volunteers. Reg Anesth Pain Med. 28(4):289-293.
Ginsberg F, et al. (1991) Double-blind, randomized crossover study of the percutaneous efficacy and tolerability of a topical indomethacin spray versus placebo in the treatment of tendinitis. J Int Med Res. 19(2):131-136.
Guindon J, et al. (2007) Recent advances in the pharmacological management of pain. Drugs. 67(15):2121-2133. (Abstract Only).
Gupta NK, et al. (2013) Randomized controlled trial of topical EMLA and breastfeeding for reducing pain during wDPT vaccination. Eur J Pediatr. 172(11): 1527-1533.
Gursoy A, et al. (2007) the analgesic efficacy of lidocaine/prilocaine (EMLA) cream during fine-needle aspiration biopsy of thyroid nodules. Clin Endocrinol (Oxf). 66(5):691-694.
Heir G, et al. (2008) Use of topical medication in orofacial neuropathic pain: a retrospective study. Oral Surg Oral Med Oral Pathol Oral Radiol Endod. 105(4):466-469. (Abstract Only).
Hirsh I, et al. (2007) Tramadol improves patients' tolerance of transrectal ultrasound-guided prostate biopsy. Urology. 69(3):491-494.
Hong JP, et al. (2014) Comparison of analgesic effect of preoperative topical diclofenac and ketorolac on postoperative pain after photorefractive keratectomy. J Cataract Refract Surg. 40(10):1689-1696.
Hong JY, et al. (2003) Suprascapular nerve block or a piroxicam patch for shoulder tip pain after day case laparoscopic surgery. Eur J Anaesthesiol. 20(3):234-8. Erratum in: Eur J Anaesthesiol. (2003) 20(5):426. (Abstract Only).
Hopp C, et al. (2012) Clinical efficacy of tetracaine anesthetic paste. Gen Dent. 60(2):e69-73. (Abstract Only).
Hui-Chen F, et al. (2013) The effect of EMLA cream on minimizing pain during venipuncture in premature infants. J Trop Pediatr. 59(1):72-73.
Keppel Hesselink JM, et al. (2013) Treatment of chronic regional pain syndrome type 1 with palmitoylethanolamide and topical ketamine cream: modulation of nonneuronal cells. J Pain Res. 6:239-245.
Kneer W, et al. (2009) A multiple-dose, open-label, safety, compliance, and usage evaluation study of epicutaneously applied Diractin (ketoprofen in Transfersome) in joint/musculoskeletal pain or soft tissue inflammation. Curr Drug Saf. 4(1):5-10.

(56) References Cited

OTHER PUBLICATIONS

Kolesnikov Y, et al. (2008) Analgesic synergy between topical opioids and topical non-steroidal anti-inflammatory drugs in the mouse model of thermal pain. Eur J Pharmacol. 579(1-3):126-133. (Abstract Only).
Kronenberg RH. (2002) Ketamine as an analgesic: parenteral, oral, rectal, subcutaneous, transdermal and intranasal administration. J Pain Palliat Care Pharmacother. 16(3):27-35. (Abstract Only).
Kwon YS, et al. (2012) Treatment for postoperative wound pain in gynecologic laparoscopic surgery: topical lidocaine patches. J Laparoendosc Adv Surg Tech A. 22(7):668-673.
Lee HJ, et al. (2013) The effect of buffered lidocaine in local anesthesia: a prospective, randomized, double-blind study. J Hand Surg Am. 38(5):971-975.
Lehman JS, et al. (2008) Effective use of topical amitriptyline hydrochloride 2.5% and ketamine hydrochloride 0.5% for analgesia in refractory proctodynia. J Drugs Dermatol. 7(9):887-889. (Abstract Only).
Lehmann HA, et al. (1996) Meloxicam: A toxicology overview. InflammoPharmacology. 4(2):105-123. (Abstract Only).
Liang CL, et al. (2011) Topical anesthetic EMLA for postoperative wound pain in stereotactic gamma knife radiosurgery: a perspective, randomized, placebo-controlled study. Minim Invasive Neurosurg. 54(2):75-78.
Liberty G, et al. (2007) Lidocaine-prilocaine (EMLA) cream as analgesia for hysterosalpingography: a prospective, randomized, controlled, double blinded study. Hum Reprod. 22(5):1335-1339.
Lynch ME, et al. (2003) A pilot study examining topical amitriptyline, ketamine, and a combination of both in the treatment of neuropathic pain. Clin J Pain. 19(5):323-328.
Lynch ME, et al. (2005) Topical 2% amitriptyline and 1% ketamine in neuropathic pain syndromes: a randomized, double-blind, placebo-controlled trial. Anesthesiology. 103(1):140-146.
Lynch ME, et al. (2005) Topical amitriptyline and ketamine in neuropathic pain syndromes: an open-label study. J Pain. 6(10):644-649.
Machen J, et al. (2002) Efficacy of a proprietary ibuprofen gel in soft tissue injuries: a randomised, double-blind, placebo-controlled study. Int J Clin Pract. 56(2):102-106.
Mansell-Gregory M, et al. (1998) Randomised double blind trial of Emla for the control of pain related to cryotherapy in the treatment of genital HPV lesions. Sex Transm Infect. 74(4):274-275.
Marks R, et al. (1994) Plasma and cutaneous drug levels after topical application of piroxicam gel: a study in healthy volunteers. Skin Pharmacol. 7(6):340-344. (Abstract Only).
Martens M. (1997) Efficacy and tolerability of a topical NSAID patch (local action transcutaneous flurbiprofen) and oral diclofenac in the treatment of soft-tissue rheumatism. Clin Rheumatol. 16(1):25-31.
Matucci-Cerinic M, et al. (1988) Ketoprofen vs etofenamate in a controlled double-blind study: evidence of topical effectiveness in soft tissue rheumatic pain. Int J Clin Pharmacol Res. 8(3):157-160. (Abstract Only).
Mazières B, et al. (2005) Topical ketoprofen patch (100 mg) for the treatment of ankle sprain: a randomized, double-blind, placebo-controlled study. Am J Sports Med. 33(4):515-523.
Mazières B, et al. (2005) Topical ketoprofen patch in the treatment of tendinitis: a randomized, double blind, placebo controlled study. J Rheumatol. 32(8):1563-1570.
Mazières B. (2005) Topical ketoprofen patch. Drugs R D. 6(6):337-344. (Abstract Only).
Merskey H. (1997) Pharmacological approaches other than opioids in chronic non-cancer pain management. Acta Anaesthesiol Scand. 41(1 Pt 2):187-190. (Abstract Only).
Missotten L, et al. (2001) Topical 0.1% indomethacin solution versus topical 0.1% dexamethasone solution in the prevention of inflammation after cataract surgery. The Study Group. Ophthalmologica. 215(1):43-50.
Moen MD. (2009) Topical diclofenac solution. Drugs. 69(18):2621-2632.

Moghadamnia AA, et al. (2009) Evaluation of the effect of locally administered amitriptyline gel as adjunct to local anesthetics in irreversible pulpitis pain. Indian J Dent Res. 20(1):3-6. (Abstract Only).
Momo K, et al. (2005) Preparation and clinical application of indomethacin gel for medical treatment of stomatitis. Yakugaku Zasshi. 125(5):433-440.
Moretti Md, et al. (2000) In vitro release and antiinflammatory activity of topical formulations of ketoprofen. Boll Chim Farm. 139(2):67-72. (Abstract Only).
Nahata MC, et al. (1999) Stability of lamotrigine in two extemporaneously prepared oral suspensions at 4 and 25 degrees C. Am J Health Syst Pharm. 56(3):240-242. (Abstract Only).
Nayak R, et al. (2006) Evaluation of three topical anaesthetic agents against pain: a clinical study. Indian J Dent Res. 17(4):155-160.
Okon T. (2007) Ketamine: an introduction for the pain and palliative medicine physician. Pain Physician. 10(3):493-500.
Oskouee SJ, et al. (2007) Bandage contact lens and topical indomethacin for treating persistent corneal epithelial defects after vitreoretinal surgery. Cornea. 26(10):1178-1181.
Park ES, et al. (2005) Transdermal delivery of piroxicam using microemulsions. Arch Pharm Res. 28(2):243-248. (Abstract Only).
Patel RK, et al. (1996) Comparison of ketoprofen, piroxicam, and diclofenac gels in the treatment of acute soft-tissue injury in general practice. General Practice Study Group. Clin Ther. 18(3):497-507.
PCCA (Fall 2011) T3 Sodium Dilution (1:1000). Issue 1, p. 35.
Pelfini C, et al. (1989) Flurbiprofen in gel: study of acceptability, tolerability and evaluation of its allergenic potential. G Ital Dermatol Venereol. 124(9):XLIII-XLVI.
Peniston JH, et al. (2012) Long-term tolerability of topical diclofenac sodium 1% gel for osteoarthritis in seniors and patients with comorbidities. Clin Interv Aging. 7:517-523.
Pénzes T, et al. (2005) Topical absorption of piroxicam from organogels—i n. vitro and in vivo correlations. Int J Pharm. 298(1):47-54.
Pharmacy OneSource. Simplifi 797—USP Chapter 797 Compliance Management (2 pages), Available at http://www.pharmacyonesource.com/simplifi797/.
Picazo A, et al. (2006) Examination of the interaction between peripheral diclofenac and gabapentin on the 5% formalin test in rats. Life Sci. 79(24):2283-2287.
Poterucha TJ, et al. (2013) Topical amitriptyline combined with ketamine for the treatment of erythromelalgia: a retrospective study of 36 patients at Mayo Clinic. J Drugs Dermatol. 12(3):308-310.
Pöyhiä R, et al. (2006) Topically administered ketamine reduces capsaicin-evoked mechanical hyperalgesia. Clin J Pain. 22(1):32-36.
Predel HG, et al. (2012) Efficacy and safety of diclofenac diethylamine 2.32% gel in acute ankle sprain. Med Sci Sports Exerc. 44(9):1629-1636.
Predel HG, et al. (2013) A randomized, double-blind, placebo-controlled multicentre study to evaluate the efficacy and safety of diclofenac 4% spray gel in the treatment of acute uncomplicated ankle sprain. J Int Med Res. 41(4):1187-1202.
Prommer EE. (2009) Topical analgesic combinations for bortezomib neuropathy. J Pain Symptom Manage. 37(3):e3-5.
Rahimi M, et al. (2012) Comparison of topical anesthetic cream (EMLA) and diclofenac suppository for pain relief after hemorrhoidectomy: a randomized clinical trial. Surg Today. 42(12):1201-1205.
Rao RD, et al. (2008) Efficacy of lamotrigine in the management of chemotherapy-induced peripheral neuropathy: a phase 3 randomized, double-blind, placebo-controlled trial, NO1C3. Cancer. 112(12):2802-2808.
Rashwana S, et al. (2014) Effect of tramadol gargle on postoperative sore throat: A double blinded randomized placebo controlled study. Egyptian J Anaesthesia. 30(3): 235-239.
Renno Si, et al. (2006) the efficacy of lamotrigine in the management of chemotherapy-induced peripheral neuropathy: A phase III randomized, double blind, placebo-controlled NCCTG trial, NO1C3. J Clin Oncol. 24(185):530. (Abstract Only).

(56) References Cited

OTHER PUBLICATIONS

Ritchie LD. (1996) A clinical evaluation of flurbiprofen LAT and piroxicam gel: a multicentre study in general practice. Clin Rheumatol. 15(3):243-247. (Abstract Only).
Roth SH, et al. (2014) Efficacy and safety of a topical diclofenac solution (pennsaid) in the treatment of primary osteoarthritis of the knee: a randomized, double-blind, vehicle-controlled clinical trial. Arch Intern Med. 164(18):2017-2023.
Rother M, et al. (2013) A randomized, double-blind, phase III trial in moderate osteoarthritis knee pain comparing topical ketoprofen gel with ketoprofen-free gel. J Rheumatol. 40(10):1742-1748.
Rovenský J, et al. (2001) Treatment of knee osteoarthritis with a topical non-steroidal antiinflammatory drug. Results of a randomized, double-blind, placebo-controlled study on the efficacy and safety of a 5% ibuprofen cream. Drugs Exp Clin Res. 27(5-6):209-221.
Rowbotham MC, et al. (1995) Topical lidocaine gel relieves postherpetic neuralgia. Ann Neurol. 37(2):246-253. (Abstract Only).
Russell AL. (1991) Piroxicam 0.5% topical gel compared to placebo in the treatment of acute soft tissue injuries: a double-blind study comparing efficacy and safety. Clin Invest Med. 14(1):35-43. (Abstract Only).
Sakai T, et al. (2004) Quantitative and selective evaluation of differential sensory nerve block after transdermal lidocaine. Anesth Analg. 98(1):248-251.
Samson D, et al. (2007) Eutectic mixture of local anesthetic (EMLA) decreases pain during humeral block placement in nonsedated patients. Anesth Analg. 105(2):512-515.
Sanabria MR, et al. (2013) Ocular pain after intravitreal injection. Curr Eye Res. 38(2):278-282.
Sandroni P, et al. (2006) Combination gel of 1% amitriptyline and 0.5% ketamine to treat refractory erythromelalgia pain: a new treatment option? Arch Dermatol. 142(3):283-286. (Abstract Only).
Sanosil. (2010) Sanosil Product Description Sheet. (7 pages).
Sawynok J, et al. (1999) Peripheral antinociceptive actions of desipramine and fluoxetine in an inflammatory and neuropathic pain test in the rat. Pain. 82(2):149-158. (Abstract Only).
Scott MA, et al. (1999) Use of transdermal amitriptyline gel in a patient with chronic pain and depression. Pharmacotherapy. 19(2):236-239. (Abstract Only).
Segatto MM, et al. (2013) Comparative study of actinic keratosis treatment with 3% diclofenac sodium and 5% 5-fluorouracil. An Bras Dermatol. 88(5):732-738.
Shimoda O, et al. (1993) Transdermal application of 10% lidocaine-gel for management of pain associated with herpes zoster. Masui. 42(8):1171-1176. (Abstract Only).
Sick Kids Pharmacy Order Form for Baclofen (5 mg/mL Oral Suspension) (Apr. 2007) (1 page).
Simon LS, et al. (2009) Efficacy and safety of topical diclofenac containing dimethyl sulfoxide (DMSO) compared with those of topical placebo, DMSO vehicle and oral diclofenac for knee osteoarthritis. Pain. 143(3):238-245.
Slatkin NE, et al.(2003) Topical ketamine in the treatment of mucositis pain. Pain Med. 4(3):298-303.
Suresh DK, et al. (2001) Intracrevicular application of 0.3% Flurbiprofen gel and 0.3% Triclosan gel as anti inflammatory agent. A comparative clinical study. Indian J Dent Res. 12(2):105-112. (Abstract Only).
Taddio A, et al. (2002) Lidocaine-prilocaine cream versus tetracaine gel for procedural pain in children. Ann Pharmacother. 36(4):687-692.
Tekelioglu UY, et al. (2013) Comparison of topical tramadol and ketamine in pain treatment after tonsillectomy. Paediatr Anaesth. 23(6):496-501.
Thaller VT, et al. (2000) The effect of pre-operative topical flurbiprofen or diclofenac on pupil dilatation. Eye (Lond). 14 ( Pt 4):642-645.
Tham EJ, et al. (1994) An assessment of prilocaine as a topical anaesthetic agent for fibreoptic bronchoscopy in comparison with lidocaine. Acta Anaesthesiol Scand. 38(5):442-447.
Tiso RL, et al. (2010) Oral versus topical Ibuprofen for chronic knee pain: a prospective randomized pilot study. Pain Physician. 13(5):457-467.
Titlic M, et al. (2008) Lamotrigine in the treatment of pain syndromes and neuropathic pain. Bratisl Lek Listy. 109(9):421-424. (Abstract Only).
Toker Mi, et al. (2006) The effects of topical ketorolac and indomethacin on measles conjunctivitis: randomized controlled trial. Am J Ophthalmol. 141(5):902-905.
Trnaský K, et al. (2004) Efficacy and safety of 5% ibuprofen cream treatment in knee osteoarthritis. Results of a randomized, double-blind, placebo-controlled study. J Rheumatol. 31(3):565-572.
Underwood M, et al. (2008) Topical or oral ibuprofen for chronic knee pain in older people. The TOIB study. Health Technol Assess. 12(22):iii-iv, ix-155.
United States Pharmacopeial Convention (2008) No. 1231—Water for Pharmaceutical Purposes (50 pages).
United States Pharmacopeial Convention. (2013) Official Monograph for Lidocaine and Prilocaine Cream. USP 36: 4115-4117. (3 pages).
United States Pharmacopeial Convention. (2013) Official Monograph for Meloxicam Tablets. USP 36: 4230-4231. (2 pages).
United States Pharmacopeial Convention. (2013) Official Monograph for Topiramate. USP 36: 5431-5434. (4 pages).
Vadivelu N, et al. (2010) Recent advances in postoperative pain management. Yale J Biol Med. 83(1):11-25.
Vranken JH. (2009) Mechanisms and treatment of neuropathic pain. Cent Nery Syst Agents Med Chem. 9(1):71-78. (Abstract Only).
Whitefield M, et al. (2002) Comparative efficacy of a proprietary topical ibuprofen gel and oral ibuprofen in acute soft tissue injuries: a randomized, double-blind study. J Clin Pharm Ther. 27(6):409-417.
Wiffen PJ, et al. (2007) Lamotrigine for acute and chronic pain. Cochrane Database Syst Rev. (2):CD006044. (Abstract Only).
Wiffen PJ, et al. (2011) Lamotrigine for acute and chronic pain. Cochrane Database Syst Rev. (2):CD006044. Update in Wiffen PJ, et al. (2013) Lamotrigine for chronic neuropathic pain and fibromyalgia in adults. Cochrane Database Syst Rev. 12:CD006044.
Wiffen PJ, et al. (2013) Topiramate for neuropathic pain and fibromyalgia . In adults. Cochrane Database Syst Rev. 8:CD008314.
Wyllie MG, et al. (2012) The role of local anaesthetics in premature ejaculation. BJU Int. 110(11 Pt C):E943-E948.
Yavas GF, et al. (2007) Preoperative topical indomethacin to prevent pseudophakic cystoid macular edema. J Cataract Refract Surg. 33(5):804-807.
Yeoh, et al. (2012) Pain during venous cannulation: Double-blind, randomized clinical trial of analgesic effect between topical amethocaine and eutectic mixture of local anesthetic. J Anaesthesiol Clin Pharmacol. 28(2):205-209.
Zacher J, et al. (2008) Topical diclofenac and its role in pain and inflammation: an evidence-based review. Curr Med Res Opin. 24(4):925-950. (Abstract Only).
Notice of Abandonment dated Mar. 28, 2013 for U.S. Appl. No. 13/337,598, filed Dec. 27, 2011 (Inventor: Jay Richard Ray II) (2 pages).
Express Abandonment to Obtain a Refund filed Mar. 22, 2013 for U.S. Appl. No. 13/337,598, filed Dec. 27, 2011 (Inventor: Jay Richard Ray II) (1 page).
Decision on Petition dated Nov. 14, 2012 for U.S. Appl. No. 13/337,598, filed Dec. 27, 2011 (Inventor: Jay Richard Ray II) (1 page).
Petition for Express Abandonment to Obtain a Refund filed Nov. 6, 2012 for U.S. Appl. No. 13/337,598, filed Dec. 27, 2011 (Inventor: Jay Richard Ray II) (1 page).
Restriction Requirement dated Nov. 2, 2012 for U.S. Appl. No. 13/337,598, filed Dec. 27, 2011 (Inventor: Jay Richard Ray II) (9 pages).
Notice of Abandonment dated Aug. 6, 2012 for U.S. Appl. No. 13/409,738, filed Mar. 1, 2012 (Inventor: Jay Richard Ray II) (2 pages).
Decision on Petition dated Aug. 6, 2012 for U.S. Appl. No. 13/409,738, filed Mar. 1, 2012 (Inventor: Jay Richard Ray II) (1 page).

(56) References Cited

OTHER PUBLICATIONS

Petition for Express Abandonment to Obtain a Refund filed Aug. 1, 2012 for U.S. Appl. No. 13/409,738, filed Mar. 1, 2012 (Inventor: Jay Richard Ray II) (1 page).
**Non-Final Office Action dated Nov. 27, 2015 for U.S. Appl. No. 13/448,088, filed Apr. 16, 2012 (Inventor: Jay Richard Ray II) (19.
**Response filed Aug. 6, 2015 for U.S. Appl. No. 13/448,088, filed Apr. 16, 2012 (Inventor: Jay Richard Ray II) (20 pages).
**Non-Final Office Action dated Apr. 7, 2015 for U.S. Appl. No. 13/448,088, filed Apr. 16, 2012 (Inventor: Jay Richard Ray II) (21.
**Response filed May 27, 2014 for U.S. Appl. No. 13/448,088, filed Apr. 16, 2012 (Inventor: Jay Richard Ray II) (12 pages).
**Final Office Action dated Feb. 25, 2014 for U.S. Appl. No. 13/448,088 filed Apr. 16, 2012 (Inventor: Jay Richard Ray II) (13 pages).
**Response filed Nov. 4, 2013 for U.S. Appl. No. 13/448,088, filed Apr. 16, 2012 (Inventor: Jay Richard Ray II) (12 pages).
**Non-Final Office Action dated May 2, 2013 for U.S. Appl. No. 13/448,088, filed Apr. 16, 2012 (Inventor: Jay Richard Ray II) (14.
**Response filed Mar. 04, 2013 for U.S. Appl. No. 13/448,088, filed Apr. 16, 2012 (Inventor: Jay Richard Ray II) (13 pages).
**Non-Final Office Action dated Dec. 31, 2012 for U.S. Appl. No. 13/448,088, filed Apr. 16, 2012 (Inventor: Jay Richard Ray II) (10.
**Response to Restriction Requirement filed Oct. 26, 2012 for U.S. Appl. No. 13/448,088, filed Apr. 16, 2012 (Inventor: Jay Richard Ray II) (9 pages).
**Restriction Requirement dated Sep. 26, 2012 for U.S. Appl. No. 13/448,088, filed Apr. 16, 2012 (Inventor: Jay Richard Ray II) (6 pages).
Non-Final Office Action dated Mar. 4, 2016 for U.S. Appl. No. 13/564,525, filed Aug. 1, 2012 (Inventor: Jay Richard Ray II) (22 pages).
Advisory Action with AFCP 2.0 Decision dated Jul. 27, 2015 for U.S. Appl. No. 13/564,525 filed Aug. 1, 2012 (Inventor: Jay Richard Ray II) (4 pages).
Response with AFCP 2.0 Request filed Jul. 17, 2015 for U.S. Appl. No. 13/564,525 filed Aug. 1, 2012 (Inventor: Jay Richard Ray II) (11 pages).
Final Office Action dated Jun. 9, 2015 for U.S. Appl. No. 13/564,525, filed Aug. 1, 2012 (Inventor: Jay Richard Ray II) (18 pages).
Response filed May 12, 2015 for U.S. Appl. No. 13/564,525, filed Aug. 1, 2012 (Inventor: Jay Richard Ray II) (10 pages).
Non-Final Office Action dated Feb. 12, 2015 for U.S. Appl. No. 13/564,525, filed Aug. 1, 2012 (Inventor: Jay Richard Ray II) (12 pages).
Terminal Disclaimer filed Sep. 26, 2014 and Approval for U.S. Appl. No. 13/564,525, filed Aug. 1, 2012 (Inventor: Jay Richard Ray II) (3 pages).
Response filed Nov. 4, 2013 for U.S. Appl. No. 13/564,525, filed Aug. 1, 2012 (Inventor: Jay Richard Ray II) (10 pages).
Terminal Disclaimer filed Sep. 30, 2013 and Disapproval for U.S. Appl. No. 13/564,525, filed Aug. 1, 2012 (Inventor: Jay Richard Ray II) (3 pages).
Final Office Action dated May 23, 2013 for U.S. Appl. No. 13/564,525, filed Aug. 1, 2012 (Inventor: Jay Richard Ray II) (19 pages).
Response filed Apr. 16, 2013 for U.S. Appl. No. 13/564,525, filed Aug. 1, 2012 (Inventor: Jay Richard Ray II) (14 pages).
Non-Final Office Action dated Jan. 18, 2013 for U.S. Appl. No. 13/564,525, filed Aug. 1, 2012 (Inventor: Jay Richard Ray II) (14 pages).
Response to Restriction Requirement filed Dec. 3, 2012 for U.S. Appl. No. 13/564,525, filed Aug. 1, 2012 (Inventor: Jay Richard Ray II) (9 pages).
Restriction Requirement dated Nov. 2, 2012 for U.S. Appl. No. 13/564,525, filed Aug. 1, 2012 (Inventor: Jay Richard Ray II) (9 pages).
Response filed Nov. 24, 2015 for U.S. Appl. No. 14/609,063, filed Nov. 14, 2015 (Inventor: Jay Richard Ray II) (20 pages).

Non-Final Office Action dated Aug. 27, 2015 for U.S. Appl. No. 14/609,063, filed Nov. 14, 2015 (Inventor: Jay Richard Ray II) (15 pages).
Response to Restriction Requirement filed Jun. 4, 2015 for U.S. Appl. No. 14/609,063, filed Nov. 14, 2015 (Inventor: Jay Richard Ray II) (9 pages).
Restriction Requirement dated May 13, 2015 for U.S. Appl. No. 14/609,063, filed Nov. 14, 2015 (Inventor: Jay Richard Ray II) (5 pages).
Preliminary Amendment filed Feb. 19, 2015 for U.S. Appl. No. 14/609,063, filed Nov. 14, 2015 (Inventor: Jay Richard Ray II) (9 pages).
Non-Final Office Action dated Feb. 9, 2016 for U.S. Appl. No. 14/836,455, filed Aug. 26, 2015 (Inventor: Jay Richard Ray II) (8 pages).
Response to Restriction Requirement filed Jan. 7, 2016 for U.S. Appl. No. 14/836,455, filed Aug. 26, 2015 (Inventor: Jay Richard Ray II) (2 pages).
Restriction Requirement dated Dec. 10, 2015 for U.S. Appl. No. 14/836,455, filed Aug. 26, 2015 (Inventor: Jay Richard Ray II) (6 pages).
Restriction Requirement dated Jan. 29, 2016 for U.S. Appl. No. 14/836,491, filed Aug. 26, 2015 (Inventor: Jay Richard Ray II) (6 pages).
Response to Restriction Requirement filed Mar. 4, 2016 for U.S. Appl. No. 14/836,509, filed Aug. 26, 2015 (published as WO 2013/101949).
Restriction Requirement dated Jan. 6, 2016 for U.S. Appl. No. 14/836,509, filed Aug. 26, 2015 (published as WO 2013/101949) (Inventor: Jay Richard Ray II) (7 pages).
International Search Report dated Mar. 5, 2013 for International Patent Application No. PCT/US12/71846 filed Dec. 27, 2012 (published as WO 2013/101949) (Applicant: JCDS Holdings, LLC) (4 pages).
Written Opinion dated Mar. 5, 2013 for International Patent Application No. PCT/US12/71846 filed Dec. 27, 2012 (published as WO 2013/101949) (Applicant: JCDS Holdings, LLC) (7 pages).
International Preliminary Report on Patentability dated May 5, 2015 for International Patent Application No. PCT/US12/71846 filed Dec. 27, 2012 (published as WO 2013/101949) (Applicant: JCDS Holdings, LLC) (7 pages).
International Search Report dated Feb. 23, 2012 for International Patent Application No. PCT/US2011/054324 filed Sep. 30, 2011 (published as WO 2013/048453) (Applicant: Jay Richard Ray, II) (3 pages).
Written Opinion dated Feb. 23, 2012 for International Patent Application No. PCT/US2011/054324 filed Sep. 30, 2011 (published as WO 2013/048453) (Applicant: Jay Richard Ray, II) (6 pages).
International Preliminary Report on Patentability dated Apr. 1, 2014 for International Patent Application No. PCT/US2011/054324 filed Sep. 30, 2011 (Published as WO 2013/048453)(Applicant: Jay Richard Ray, II)(7 pages).
Restriction Requirement dated Jul. 18, 2012 for U.S. Appl. No. 13/328,369, filed Dec. 16, 2011 (Inventor: Jay Richard Ray II) (6 pages).
Response to Restriction Requirement filed Aug. 2, 2012 for U.S. Appl. No. 13/328,369, filed Dec. 16, 2011 (Inventor: Jay Richard Ray II) (2 pages).
Non-Final Office Action dated Oct. 4, 2012 for U.S. Appl. No. 13/328,369, filed Dec. 16, 2011 (Inventor: Jay Richard Ray II) (7 pages).
Response filed Dec. 18, 2012 for U.S. Appl. No. 13/328,369, filed Dec. 16, 2011 (Inventor: Jay Richard Ray II) (11 pages).
Final Office Action dated Jan. 14, 2013 for U.S. Appl. No. 13/328,369, filed Dec. 16, 2011 (Inventor: Jay Richard Ray II) (10 pages).
Response filed Mar. 22, 2013 for U.S. Appl. No. 13/328,369, filed Dec. 16, 2011 (Inventor: Jay Richard Ray II) (11 pages).
Non-Final Office Action dated Feb. 5, 2014 for U.S. Appl. No. 13/328,369, filed Dec. 16, 2011 (Inventor: Jay Richard Ray II) (10 pages).
Response filed Jul. 7, 2014 for U.S. Appl. No. 13/328,369, filed Dec. 16, 2011 (Inventor: Jay Richard Ray II) (15 pages).

(56) References Cited

OTHER PUBLICATIONS

Final Office Action dated Oct. 6, 2014 for U.S. Appl. No. 13/328,369, filed Dec. 16, 2011 (Inventor: Jay Richard Ray II) (10 pages).
Examiner Interview Summary dated Dec. 2, 2014 for U.S. Appl. No. 13/328,369, filed Dec. 16, 2011 (Inventor: Jay Richard Ray II) (2 pages).
Notice of Appeal filed Feb. 6, 2015 for U.S. Appl. No. 13/328,369, filed Dec. 16, 2011 (Inventor: Jay Richard Ray II) (1 page).
Response filed Apr. 3, 2015 for U.S. Appl. No. 13/328,369, filed Dec. 16, 2011 (Inventor: Jay Richard Ray II) (10 pages).
Appeal Brief filed Apr. 6, 2015 for U.S. Appl. No. 13/328,369, filed Dec. 16, 2011 (Inventor: Jay Richard Ray II) (30 pages).
Advisory Action dated Apr. 17, 2015 for U.S. Appl. No. 13/328,369, filed Dec. 16, 2011 (Inventor: Jay Richard Ray II) (3 pages).
Examiner's Answer dated Sep. 16, 2015 for U.S. Appl. No. 13/328,369, filed Dec. 16, 2011 (Inventor: Jay Richard Ray II) (9 pages).
Reply Brief filed Oct. 29, 2015 for U.S. Appl. No. 13/328,369, filed Dec. 16, 2011 (Inventor: Jay Richard Ray II) (10 pages).
Docketing Notice dated Nov. 17, 2015 for U.S. Appl. No. 13/328,369, filed Dec. 16, 2011 (Inventor: Jay Richard Ray II) (2 pages).

\* cited by examiner

COMPOSITION AND METHOD FOR COMPOUNDED THERAPY

CROSS-REFERENCE TO RELATED APPLICATIONS

This patent application is a continuation in-part of co-pending U.S. patent application Ser. No. 13/448,088, entitled Composition and Method for Compounded Therapy, filed Apr. 16, 2012, which is a continuation of U.S. patent application Ser. No. 13/409,738, entitled Composition and Method for Compounded Therapy, filed Mar. 1, 2012, now abandoned, which is a continuation-in-part of U.S. patent application Ser. No. 13/337,598, entitled Composition and Method for Compounded Therapy, filed Dec. 27, 2011, now abandoned.

FIELD OF THE INVENTION

The present application relates to compounded therapies. In particular, the present application relates to compositions for compounded therapy and methods of compounding medications.

BACKGROUND

Transdermal creams are employed to deliver medication to the skin of a patient. Conventional compositions intended for topical administration include EMLA cream, a eutectic mixture of lidocaine and prilocaine in an emulsified topical cream, such as disclosed by U.S. Pat. Nos. 6,299,902 and 4,562,060, which are incorporated herein by reference in their entireties. However, conventional transdermal creams may include various drawbacks, such as addressing limited medical conditions, creating adverse side effects, and/or having limited shelf lives. Additionally, conventional methods of manufacturing transdermal creams may be inefficient and/or lack precision with the amount of active ingredients, or have other drawbacks.

SUMMARY

In one aspect, a method of producing a compounded medication comprises formulating a compounded transdermal cream. Formulating the compounded transdermal cream may comprise combining a first component and a second component, and mixing the combined first component and second component. The first component may comprise a diclofenac sodium solution comprising diclofenac, DMSO, propylene glycol, purified water, and at least one of glycerin or hydroxypropyl cellulose. The second component may comprise a lidocaine and prilocaine cream comprising lidocaine, prilocaine, polyoxyethylene fatty acid esters, sodium hydroxide, purified water, and at least one of carboxypolymethylene or carbomer 934. The first component and the second component may be combined in amounts such that the compounded transdermal cream comprises diclofenac in an amount between approximately 0.1% and approximately 0.75% by weight of the compounded transdermal cream and approximately equivalent amounts of each of lidocaine and prilocaine between approximately 1.5% and approximately 2.25% by weight of the compounded transdermal cream.

In one formulation, the lidocaine an prilocaine cream is a commercially manufactured lidocaine 2.5% and prilocaine 2.5% cream. In another formulation, the diclofenac sodium solution is at least one of a commercially manufactured diclofenac sodium 1.5% solution of a commercially manufactured diclofenac sodium 2.0% solution. In one particular formulation, the lidocaine an prilocaine cream may be a commercially manufactured lidocaine 2.5% and prilocaine 2.5% cream, and the diclofenac sodium solution may be a commercially manufactured diclofenac sodium 1.5% solution, a commercially manufactured diclofenac sodium 2.0% solution, or combination thereof. The first component and the second component may be combined in amounts such that the compounded transdermal cream comprises diclofenac in an amount between approximately 0.1% and approximately 0.75%, approximately 0.1% and approximately 0.5%, or approximately 0.3% and approximately 0.75% by weight of the compounded transdermal cream. The method may further comprise packaging the compounded transdermal cream in tubes.

The method may further include combining a third component with the first and second components. The third component may be a fine powder of medication obtained from crushed tablets of one or more additional medications selected from nerve depressants, anticonvulsants, or combinations thereof. The fine powder may be combined with the first component and the second component in an amount such that the compounded transdermal cream comprises the one or more additional medications in an amount between approximately 1.0% and approximately 5.0% by weight of the cream. The one or more additional medications selected from nerve depressants, anticonvulsants, or combination thereof may be further selected from the group consisting of lamotrigine, topiramate, and gabapentin. The first component may be combined in an amount such that the compounded transdermal cream comprises approximately 0.15% by weight diclofenac. The second component may be combined in an amount such that the compounded transdermal cream comprises approximately 2.0% by weight lidocaine and approximately 2.0% by weight prilocaine. The third component may be combined in an amount such that the compounded transdermal cream comprises approximately 2.5% by weight of the additional medications.

In another aspect, a compounded transdermal cream comprises the diclofenac sodium solution added in an amount between approximately 0.1% and approximately 1% by weight of the compounded transdermal cream and lidocaine and prilocaine added or present in approximately equivalent amounts between approximately 1.5% and approximately 2.25% by weight of the compounded transdermal cream. The compounded transdermal cream may further comprise additional components such as DMSO, propylene glycol, at least one of glycerin or hydroxypropyl cellulose, polyoxyethylene fatty acid esters, sodium hydroxide, at least one of carboxypolymethylene or carbomer 934, purified water, pharmaceutically equivalent components, or combinations thereof. In one form, the diclofenac from the diclofenac sodium solution is present in an amount between approximately 0.1% and approximately 0.75% by weight of the compounded transdermal cream. In another form, the diclofenac is present in an amount between approximately 0.1% and approximately 0.5% by weight of the compounded transdermal cream. In another form, diclofenac is present in an amount between approximately 0.3% and approximately 0.75% by weight of the compounded transdermal cream.

The compounded transdermal cream may further include one or more additional medications comprising one or more nerve depressants, one or more anticonvulsants, or a combination thereof in an amount between approximately 1.0% and approximately 5.0% by weight. The one or more additional medications may be selected from the group consisting of lamotrigine, topiramate, gabapentin, and combinations thereof. In one example, diclofenac is present in an amount approximately 0.15% by weight, lidocaine is present in an amount approximately 2.0% by weight, prilocaine is present in an amount approximately 2.0% by weight, wherein the one or more additional medications is lamotrigine. In another example, diclofenac is present in an amount approximately 0.15% by weight, lidocaine is present in an amount approximately 2.0% by weight, prilocaine is present in an amount approximately 2.0% by weight, wherein the one or more additional medications is topiramate. In yet another example, diclofenac is present in an amount approximately 0.15% by weight, lidocaine is present in an amount approximately 2.0% by weight, prilocaine is present in an amount approximately 2.0% by weight, wherein the one or more additional medications is gabapentin.

The above-described and other features and advantages of the present disclosure will be appreciated and understood by those skilled in the art from the following detailed description, drawings, and appended claims.

BRIEF DESCRIPTION OF THE DRAWINGS

There is shown in the drawings embodiments which are presently preferred, it being understood, however, that the invention can be embodied in other forms without departing from the spirit or essential attributes thereof.

DETAILED DESCRIPTION OF THE INVENTION

Figure 1:
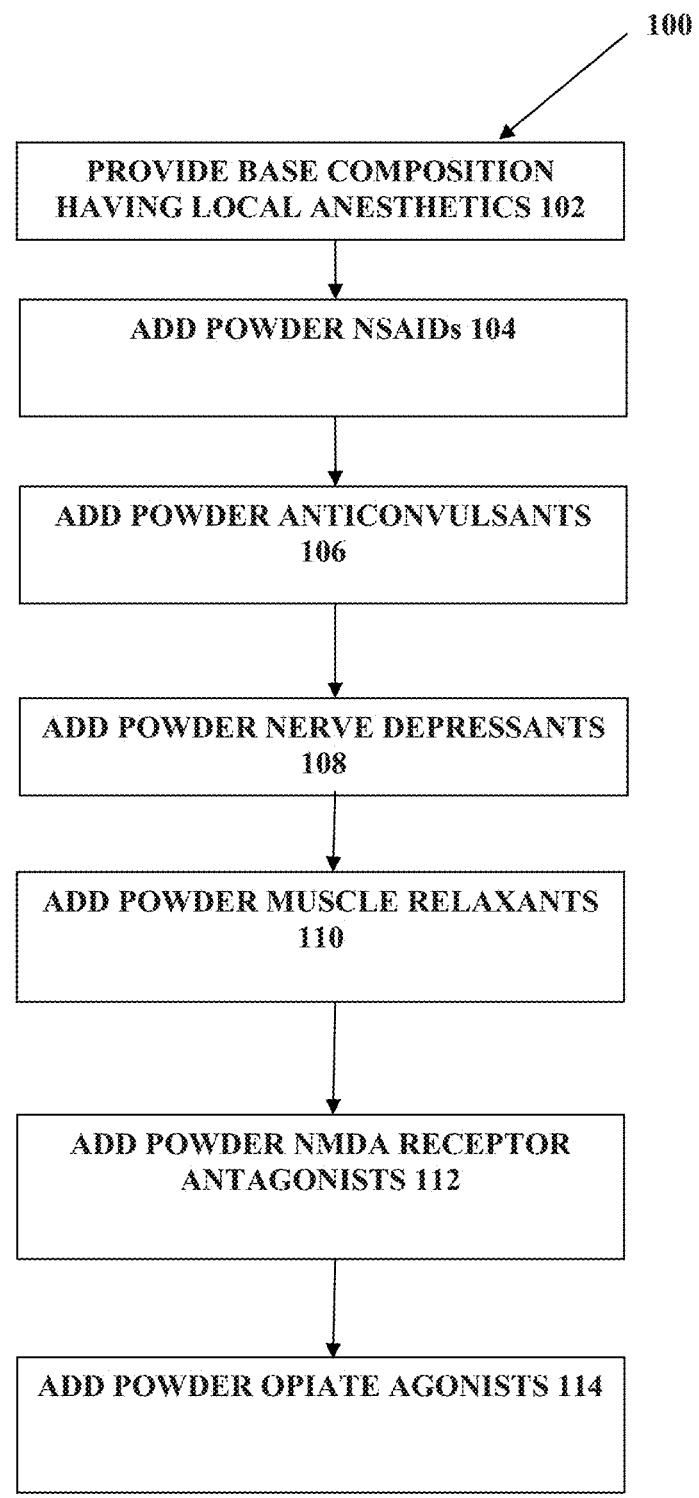
FIG. 1 depicts an exemplary method of compounding.

The present embodiments may relate to topically delivered compounded medications for treatment of various ailments, such as pain, osteoarthritis, epilepsy, inflammation, muscle fatigue, spasms, and/or other ailments. In one aspect, a transdermal cream for the effective administration of multiple medications simultaneously for one or more ailments may be provided. The transdermal cream may include low concentrations of lidocaine, prilocaine, meloxicam, lamotrigine and/or topiramate, and other active ingredients.

Alternatively, the transdermal cream may include a base having both lidocaine and prilocaine, and to which is added a fine powder of one or more medications. The medication in fine powder form may be generated from grinding up tablets of NSAIDs (Non-Steroidal Anti-Inflammatory Drugs), anticonvulsants, nerve depressants, muscle relaxants, NMDA (N-Methyl-D-aspartate) receptor antagonists, opiate or opioid agonists, antidepressants, and/or other active agents. The fine powder may allow for precise amounts of the active ingredients to be added to the base. The transdermal cream may exhibit excellent storage characteristics, and avoid separation and/or degradation of the active ingredients from the base for substantial lengths of time.

In one aspect, a transdermal cream may include lidocaine in an amount between approximately 0.5% and approximately 7.0% by weight of the transdermal cream; prilocaine in an amount between approximately 0.5% and approximately 7.0% by weight of the transdermal cream; meloxicam in an amount between approximately 0.01% and approximately 5.0% by weight of the transdermal cream; and lamotrigine and/or topiramate in an amount between approximately 0.5% and approximately 5.0% by weight of the transdermal cream. As a result, the transdermal cream may allow for the topical administration of lidocaine, prilocaine, meloxicam, and lamotrigine and/or topiramate simultaneously during use. In one embodiment, the transdermal cream may comprise approximately 2.0% by weight lidocaine and prilocaine, respectively; approximately 0.09% by weight meloxicam; and approximately 2.5% by weight either lamotrigine or topiramate.

In another aspect, a method of compounding one or more medications with a transdermal cream for the topical administration of a compounded therapy may be provided. The method may include grinding up one or more tablets of a NSAID, an anticonvulsant, a nerve depressant, a muscle relaxant, a NMDA receptor antagonist, antidepressant, and/or an opiate or opioid agonist into a fine powder of medication. The method may also include adding the fine powder of medication to a transdermal cream containing both lidocaine and prilocaine, the transdermal cream including both lidocaine and prilocaine in an amount of between approximately 0.5% and approximately 7.0% by weight of the transdermal cream. The method may include adding the fine powder of medication to the transdermal cream in a sufficient amount such that the transdermal cream includes the medication that is ground up in an amount of between approximately 0.01% and approximately 5.0% by final weight of the transdermal cream.

The fine powder may be a fine powder of compounded medication that includes two or more active ingredients. For example, the active ingredients may comprise a NSAID, such as meloxicam, and a nerve depressant or an anticonvulsant, such as lamotrigine and/or topiramate. In one embodiment, an amount of ground up compounded medication is added to the base such that the final composition of the transdermal cream after the fine powder of compounded medication is added is approximately 2.0% by weight lidocaine, approximately 2.0% by weight prilocaine, approximately 0.09% by weight meloxicam, and approximately 2.5% by weight either lamotrigine or topiramate.

I. Compositions for Compounded Therapy

The present embodiments may relate to a compounded medication program. The compounded medication program may address several ailments simultaneously. In one aspect, the present embodiments may be intended to intended to minimize skin damage or irritation caused by the topical administration of various medications. Administering low doses or applying transdermal creams or gels with low concentrations of one or more active ingredients may minimize adverse side effects, such as side effects that develop with prolonged usage.

For instance, Stevens-Johnson Syndrome (SJS) and toxic epidermal necrolysis (TEN) are two forms of life-threatening skin conditions. SJS is a potentially deadly skin disease that usually results from a drug reaction. Drugs that have been linked to SJS include, but are not limited to: NSAIDs, allopurinol, phenytoin, carbamazepine, barbiturates, anticonvulsants, and sulfa antibiotics. However, almost any drug (prescription or over-the-counter) could potentially cause SJS if a severe enough allergy is present.

The onset of severe symptoms in drug related SJS may not appear for 1-2 weeks after first taking the drug causing the allergic reaction. Initial non-specific symptoms such as coughing, aching, headaches, fevers, vomiting, and diarrhea are commonly seen. These symptoms are usually followed by a red rash across the face and trunk of the body, later followed by blisters, and in some situations the nails and hair begin to fall out.

SJS is a very serious and potentially deadly condition and should be treated accordingly. Discontinuation of the medication and treatment of the "new infection" with a suitable antibiotic is the first step. In some situations, a patient is treated in a burn unit if necessary. However, compounded therapies may administer lower doses of active agents topically, and thus the effect of any adverse skin reaction may be lowered due to the lower doses of agent that the patient is allergic to.

In view of the foregoing, the present embodiments may include providing, within a base composition, several medications that address different ailments. The medications may be mixed in low concentrations to minimize any adverse reaction to the topical cream or gel containing the several medications.

The medications may be mixed with the base composition for topical administration to a patient. The medications may include one or more local anesthetics, such as lidocaine, prilocaine, or benzocaine; one or more NSAIDs, such as meloxicam; and one or more nerve depressants and/or anticonvulsants, such as gabapentin, topiramate, or lamotrigine. The medications may also include one or more muscle relaxants, such as baclofen or cyclobenzaprine; one or more NMDA receptor antagonists, such as ketamine; and/or one or opiate or opioid agonists, such as C2 or C3 opiate agonists, or tramadol.

II. Meloxicam/Lamotrigine/Lidocaine/Prilocaine Compounded Medication

In one aspect, a transdermal cream or gel may include lidocaine, prilocaine, meloxicam, and lamotrigine. Lidocaine and prilocaine are amide-type local anesthetic agents. They may come in commercially available creams.

The amount of lidocaine and prilocaine in the transdermal cream may be approximately the same. The amount of lidocaine and prilocaine may each be between approximately 0.5% and approximately 5.0% of the total weight of the transdermal cream. Alternatively, the amount of lidocaine and prilocaine may each be between approximately 1.0% and approximately 4.0% of the total weight of the transdermal cream, or between approximately 1.5% and approximately 3.0% of the total weight of the transdermal cream. In one preferred embodiment, the amount of lidocaine and prilocaine may each be approximately 2.0% of the total weight of the final transdermal cream or gel.

Meloxicam is a NSAID that may provide pain relief, such as pain relief for osteoarthritis or rheumatoid arthritis. In one aspect, the amount of meloxicam in the transdermal cream or gel may be less than that of the other active ingredients.

The amount of meloxicam in the transdermal cream may be between approximately 0.01% and approximately 5.0% of the total weight of the transdermal cream, or between approximately 0.03% and approximately 3.0% of the total weight of the transdermal cream. Preferably, the amount of meloxicam may be between approximately 0.05% and approximately 0.15% of the total weight of the transdermal cream. In one preferred embodiment, the amount of meloxicam may be approximately 0.09% of the total weight of the transdermal cream or gel.

Lamotrigine may be characterized as an anticonvulsant. It may be used as an antiepileptic drug to treat epilepsy or bi-polar disorders. In one aspect, the amount of lamotrigine in the transdermal cream or gel may be more than the other active ingredients, such as lidocaine, prilocaine, meloxicam, and/or other active ingredients.

The amount of lamotrigine in the transdermal cream may be between approximately 0.5% and approximately 5.0% of the total weight of the transdermal cream, or between approximately 1.5% and approximately 3.5% of the total weight of the transdermal cream. Preferably, the amount of lamotrigine may be between approximately 2.0% and approximately 3.0% of the total weight of the transdermal cream. In one preferred embodiment, the amount of lamotrigine may be approximately 2.5% of the total weight of the transdermal cream or gel.

III. Meloxicam/Topiramate/Lidocaine/Prilocaine Compounded Medication

In one aspect, a transdermal cream or gel may include lidocaine, prilocaine, meloxicam, and topiramate. The amounts of lidocaine, prilocaine, and meloxicam may be as stated above. Alternatively, other amounts of lidocaine, prilocaine, and meloxicam may be used.

Topiramate may be characterized as an antiepileptic drug used to treat epilepsy or migraines. In one aspect, the amount of topiramate in the transdermal cream or gel may be more than the other active ingredients, such as lidocaine, prilocaine, meloxicam, and/or other active ingredients.

The amount of topiramate in the transdermal cream may be between approximately 0.5% and approximately 5.0% of the total weight of the transdermal cream, or between approximately 1.5% and approximately 3.5% of the total weight of the transdermal cream. Preferably, the amount of topiramate may be between approximately 2.0% and approximately 3.0% of the total weight of the transdermal cream. In one preferred embodiment, the amount of topiramate may be approximately 2.5% of the total weight of the transdermal cream or gel.

IV. Exemplary Method of Compounding

FIG. 1 depicts an exemplary method of compounding one or more medications with a transdermal cream or gel 100. The method 100 may include providing a base composition having one or more local anesthetics 102; and adding to the base a fine powder of medication comprising: one or more NSAIDs 104; one or more anticonvulsants 106; one or more or nerve depressants 108; one or more muscle relaxants 110; one or more NMDA receptor antagonists 112; and/or one or more opiate or opioid agonists 114. The transdermal cream or gel may include additional, fewer, or alternate steps and/or ingredients.

The method 100 may comprise providing a base composition 102. The base composition may comprise one or more local anesthetics 102. Primary examples of local anesthetics that the transdermal creams and base composition disclosed herein may employ include, but are not limited to, lidocaine, prilocaine, benzocaine, and/or tetracaine. The local anesthetics may comprise between approximately 0.1% and approximately 5.0% by weight of the transdermal cream. Other amounts may be used, including those discussed elsewhere herein. The base composition may include additional, fewer, or alternate ingredients.

Preferably, the base composition may include lidocaine and/or prilocaine. In one embodiment, the base composition may comprise an equal amount of lidocaine and prilocaine, such as between approximately 2.0% and approximately 3.0% by weight of the transdermal cream. Other amounts may be used, including those discussed elsewhere herein.

The method 100 may comprise adding to the base composition a fine powder of medication that includes one or more NSAIDs 104. NSAIDs may decrease inflammation, swelling, and pain. NSAIDs that may be added to the base composition may include: (1) oxicams—meloxicam and piroxicam; (2) salicylic acid derivatives—aspirin, diflunisal, salsalate, and trilisate; (3) propionic acids—flurbiprofen, ibuprofen, ketoprofen, naproxen, and oxaprozin; (4) acetic acids—diclofenac, etodolac, indomethacin, ketorolac, nabumetone, sulindac, and tolmetin; (5) fenamates—meclofenamate; and/or (6) COX-2 inhibitors—celecoxib, rofecoxib, and valdecoxib. Preferably, the final transdermal cream may comprise a low concentration of an oxicam, such as meloxicam or piroxicam, in a low amount between approximately 0.01% and 5.0% by weight of the final transdermal cream. In one embodiment, the final transdermal cream may include approximately 0.09% meloxicam by weight. Other amounts may be used, including those discussed elsewhere herein.

The method 100 may comprise adding to the base composition a fine powder of medication that includes one or more anticonvulsants 106. Anticonvulsants that may be added to the base composition may include lamotrigine and/or topiramate. The final transdermal cream may include an anticonvulsant in a low amount between approximately 0.1% and approximately 5.0% by weight of the final transdermal cream. Preferably, the final transdermal cream may comprise approximately 2.5% of either lamotrigine or topiramate by weight. Other amounts may be used, including those discussed elsewhere herein.

The method 100 may comprise adding to the base composition a fine powder of medication that includes one or more nerve depressants 108. Nerve depressants that may be added to the base composition may include gabapentin and/or others. The low amount of nerve depressant in the transdermal cream may be between approximately 0.1% and approximately 5.0% of the total weight of the transdermal cream. Other amounts may be used.

The method 100 may comprise adding to the base composition a fine powder of medication that includes one or more muscle relaxants 110. The active ingredients that may be added to the base compositions in form of fine powder may comprise baclofen, carisoprodol, chlorzoxazone, cyclobenzaprine, dantrolene, diazepam, metaxalone, methocarbamol, orphenadrine, quinine sulfate, tizanidine, and/or other muscle relaxants. The low amount of muscle relaxant in the transdermal cream may be between approximately 0.1% and approximately 5.0% of the total weight of the transdermal cream. Other amounts may be used.

The method 100 may comprise adding to the base composition a fine powder of medication that includes one or more NMDA receptor antagonists 112, such as ketamine. Ketamine may be useful because of its NMDA receptor activity (antagonism). The low amount of NMDA receptor antagonist in the transdermal cream may be between approximately 0.1% and approximately 5.0% of the total weight of the transdermal cream. Other amounts may be used.

The method 100 may comprise adding to the base composition a fine powder of medication that includes one or more opiate or opioid agonists 114. C2 opiate agonists may include oxycodone, morphine, methadone, hydromorphone, and fentanyl. C3 opiate agonists may include hydrocodone, codeine, propoxyphene, butalbital, and pentazocine. The active ingredients that may be added to the base composition in the form of fine powder may include the C2 and C3 opiate agonists named above and/or tramadol. The low amount of opiate or opioid agonist in the transdermal cream may be between approximately 0.1% and approximately 5.0% of the total weight of the transdermal cream. Other amounts may be used.

V. Another Exemplary Method of Compounding

A method of compounding medications with a base composition using a fine powder of medication is disclosed herein. In general, a base composition, such as a lidocaine/prilocaine cream, should be selected. The preparer, such as a pharmacist, should calculate the weight of powders needed. Then, the prepare should grind the medication, such as tablets containing the medication, into fine powder and weigh the ingredients. The preparer should triturate the powders together and wet with dimethyl sulfoxide (DMSO) or Sterile Water for Irrigation. The preparer should bring to total weight with the lidocaine/prilocaine cream and mix well. The mixture should be milled in an ointment mill as necessary to acquire the desired consistency. After which, the preparer should mix thoroughly and package appropriately.

Figure 2:
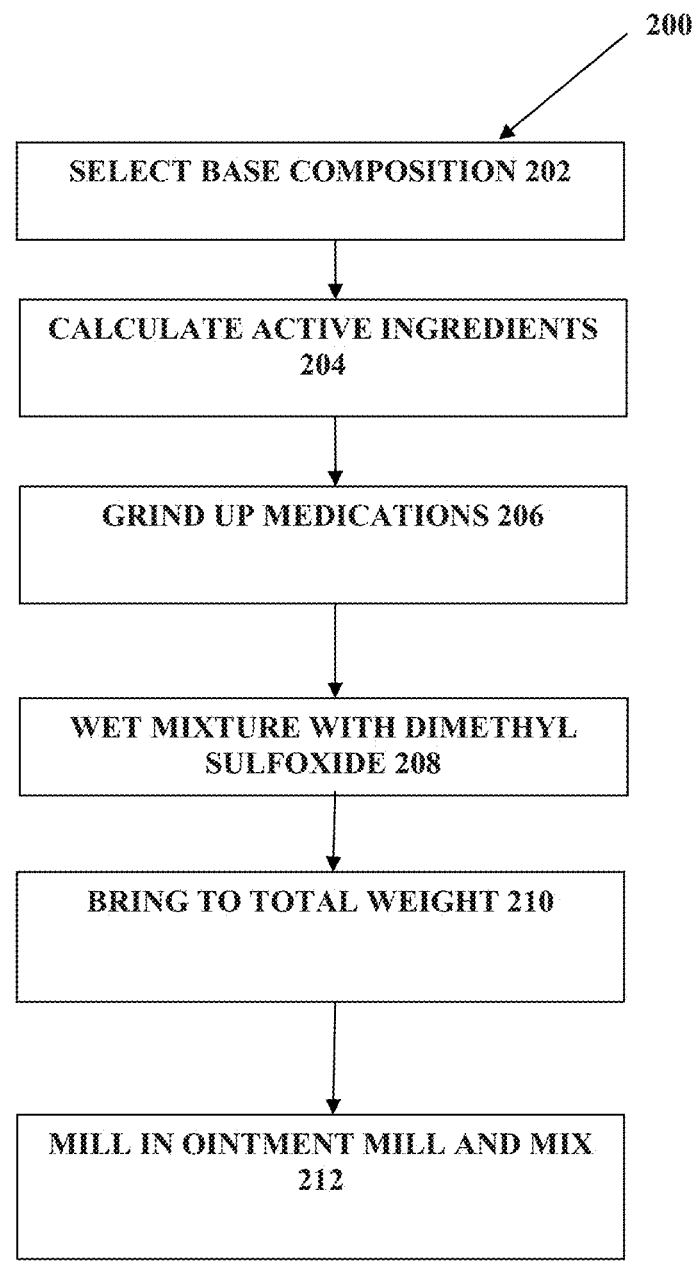
FIG. 2 depicts another exemplary method of compounding.

More specifically, FIG. 2 depicts an exemplary method of compounding medications with a transdermal cream 200. The method 200 depicted in FIG. 2 may be used to manufacture the transdermal creams discussed herein, including those discussed in relation to FIG. 1 above. The method 200 may include selecting a base composition 202; calculating an amount of active ingredients 204; grinding up the tablets containing the active ingredients 206; wetting the mixture with DMSO or Sterile Water for Irrigation 208; bringing to total weight 210; and milling in an ointment mill and mixing 212. The method 200 may include additional, fewer, or alternate actions.

The method 200 may include selecting a base composition 202 for a transdermal cream or gel. The base composition may include one or more local anesthetics, such as lidocaine and/or prilocaine. The base may include approximately equal amounts of lidocaine and prilocaine. The base composition may be a transdermal cream and may originally have approximately 2.5% lidocaine and approximately 2.5% prilocaine by weight. Other initial amounts of lidocaine and/or prilocaine may be used. In one embodiment, the base composition that includes lidocaine and/or prilocaine may be used in an amount of approximately 24,000 gm. Other amounts of base composition may be used.

The method 200 may include calculating an amount of active ingredients 204. The active ingredients may come in various size tablets. Noted herein, one of the transdermal cream embodiments, includes meloxicam and lamotrigine. For that embodiment, the ingredients may include 15 mg tablets of meloxicam, and approximately 1,500 of the 15 mg tables of meloxicam may be used. Tablets with other dosages of meloxicam may be used, and in different amounts. For instance, 7.5 mg or 30 mg tablets of meloxicam may be used.

The ingredients may also include 200 mg tablets of lamotrigine, and approximately 3,000 of the 200 mg tablets of lamotrigine may be used. Tablets with other dosages of lamotrigine may be used, and in different amounts. For instance, lamotrigine tablets ranging from 2 to 200 mg may be used.

To manufacture the transdermal cream embodiment that includes meloxicam and lamotrigine, the following formulas may be used to identify the amount of tablet powder of meloxicam and lamotrigine needed:

a. Meloxicam:

avg tab weight _____ gm×tablets needed
_____=tablet powder needed _____
gm.

b. Lamotrigine:

avg tab weight _____ gm×tablets needed
_____=tablet powder needed _____
gm.

The foregoing formulas may be used with the numbers stated above. For instance, the composition may require 1,500 of the 15 mg tables of meloxicam, and 3,000 of the 200 mg tablets of lamotrigine. As a result, in one embodiment, 22.5 grams of meloxicam and 600 grams of lamotrigine may be mixed with other ingredients, such as 24,000 gm of lidocaine 2.5%/prilocaine 2.5% cream, as well as 2,550 gm of dimethyl sulfoxide (DMSO). Instead of or in addition to lamotrigine, the medications added may include topiramate or other active ingredients. Instead of DMSO, Sterile Water for Irrigation may be used.

The method 200 may comprise grinding up the tablets containing the active ingredients 206. In one aspect, an automatic grinder may be used to grind up tablets containing one or more active ingredients into fine powder of medication. For instance, a Grindomix Mill may be used having a 100 volt, 60 Hz motor and five liter plastic container. The mill may have a standard lid, knife, and scraper. A five liter stainless steel container may be used that includes a knife holder. A knife of stainless steel may be used, and be autoclavable. The mill may have a plastic cover that is transparent.

The grinding up of the active ingredients into fine powder may allow for more precise amounts of each active ingredient in the final transdermal cream. This may be especially important when adding low amounts of active ingredients such that the final transdermal cream has low concentrations of various medications, which may reduce adverse allergic reactions to prolonged usage.

The method may include wetting the mixture with DMSO or Sterile Water for Irrigation 208. The DMSO and/or Sterile Water for Irrigation may facilitate the active ingredients penetrating the skin. After the ingredients in fine powder form are weighed, the preparer may triturate the powders of each ingredient together and wet with DMSO. For the 24,000 gm amount of lidocaine/prilocaine cream noted above, DMSO may be used in an amount of approximately 2,550 gm. Other amounts of DMSO may be used.

Instead of DMSO, the method may include wetting the mixture with only or primarily Sterile Water for Irrigation. Sterile Water for Irrigation USP may be a sterile, hypotonic, nonpyrogenic irrigating fluid or pharmaceutic aid (solvent), and may be composed of Sterile Water for Injection USP. It may be prepared by distillation and may contain no antimicrobial or bacteriostatic agents or added buffers. The pH may be about 5.7, or between 5.0 and 7.0. Sterile Water for Irrigation may be intended for use only as a single-dose, and may be classified as a sterile irrigant, wash, rinse, diluent and pharmaceutical vehicle. Instead of or addition to Sterile Water for Irrigation, Sterile Water for Injection or purified water may be used.

The method may include bringing to total weight with the lidocaine/prilocaine cream and mixing well 210. As noted elsewhere herein, after the fine powder of medication is mixed with the lidocaine/prilocaine base, the final transdermal cream may have approximately 2.0% by weight lidocaine, approximately 2.0% by weight prilocaine, approximately 0.09% by weight meloxicam, and approximately 2.5% by weight either lamotrigine or topiramate. The final transdermal cream may have other active ingredients as well, including those mentioned herein.

The method 200 may include milling the mixture in an ointment mill as necessary to acquire the desired consistency 212. After which, the preparer may mix the milled mixture thoroughly and package it in appropriate containers.

VI. Exemplary Storage Characteristics

The compounded transdermal creams discussed herein that are made using fine powder of medication may exhibit excellent storage characteristics, and avoid separation and/or degradation of the active ingredients from a base composition for substantial lengths of time, such as six months or greater. For example, Table I below depicts the results of a 198 day potency test for a transdermal cream including meloxicam, lamotrigine, lidocaine, and prilocaine. As shown, there is little degradation of the active ingredients. The sample was stored in approximately 20° C. to 25° C. (68° F. to 77° F.) conditions, and contained one large white tube with cream in a clear bag.

TABLE I

198 Day Potency Test

| Analyte/Specifications | Expected Amount | Units | Results | % of EXP. | Test Method |
|---|---|---|---|---|---|
| Lamotrigine Specifications = N/A | 2.5 | % | 2.463 | 98.5% | HPLC |
| Lidocaine Specifications = N/A | 2.0 | % | 1.927 | 96.4% | HPLC |
| Meloxicam Specifications = N/A | 0.09 | % | 0.0962 | 106.9% | HPLC |
| Prilocaine Specifications = N/A | 2.0 | % | 2.118 | 105.9% | HPLC |

Table II below depicts the results of a 100 day potency test for a transdermal cream including meloxicam, topiramate, lidocaine, and prilocaine. As shown, there is little degradation of the active ingredients. The sample was stored in approximately 20° C. to 25° C. (68° F. to 77° F.) conditions, and contained one large white tube with cream in a clear bag.

TABLE II

100 Day Potency Test

| Analyte/Specifications | Expected Amount | Units | Results | % of EXP. | Test Method |
|---|---|---|---|---|---|
| Lidocaine Specifications = N/A | 2.0 | % | 1.700 | 85.0% | HPLC |
| Meloxicam Specifications = N/A | 0.09 | % | 0.0945 | 105.0% | HPLC |
| Prilocaine Specifications = N/A | 2.0 | % | 1.899 | 95.0% | HPLC |
| Topiramate Specifications = N/A | 2.5 | % | 2.368 | 94.7% | HPLC |

VII. Exemplary Methods of Compounding Using Fine Powder

An exemplary method of compounding may include grinding up tablets of one or more active ingredients into a fine powder, and then adding those ingredients in powder form to a compounded transdermal cream or gel. The active ingredients that are ground up into a fine powder of medication may include one or more NSAIDs, anticonvulsants, nerve depressants, muscle relaxants, antidepressants, NMDA receptor antagonists, opioid or opiate agonists, local anesthetics, and/or other active agents. The transdermal cream or gel may or may not have one or more pre-existing ingredients prior to the addition of the fine powder of medication, such as one or more pre-existing local anesthetics.

The method may include grinding up tablets of one or more local anesthetics into a fine powder. The local anesthetics ground up into powder form may include lidocaine and/or prilocaine, or other agents. An amount of lidocaine and/or prilocaine powder may be added to the transdermal cream such that lidocaine comprises between approximately 0.5% and approximately 7.0% by weight of the transdermal cream, and that prilocaine comprises between approximately 0.5% and approximately 7.0% by weight of the transdermal cream. Other amounts may be used, including those discussed elsewhere herein.

The method may include grinding up tablets of one or more NSAIDs into a fine powder of medication. The NSAIDs that are ground up may include meloxicam, fluribiprofen, nabumetone, and/or other NSAIDs. The amount of NSAIDs may be between approximately 0.05% and 25.0% by weight of the transdermal cream. For instance, the transdermal cream may include meloxicam in a low amount of between approximately 0.05% and approximately 0.15% by weight of the transdermal cream, and/or flurbiprofen or nabumetone in an amount between approximately 5.0% and approximately 25.0% of the transdermal cream by weight. Other amounts may be used, including those discussed elsewhere herein.

The method may include grinding up tablets of one or more anticonvulsants into the fine powder of medication. The anticonvulsants that are ground up may include lamotrigine, topiramate, and/or other anticonvulsants. The transdermal cream may include an amount of anticonvulsant of between approximately 1.0% and approximately 5.0% by weight of the transdermal cream. Other amounts may be used, including those discussed elsewhere herein.

The method may include grinding up tablets of one or more muscle relaxants into a fine powder of medication. The muscle relaxants that are ground up may include baclofen, cyclobenzaprine, and/or other muscle relaxants. The transdermal cream may include an amount of muscle relaxant of between approximately 1.0% and approximately 5.0% by weight of the transdermal cream. Other amounts may be used, including those discussed elsewhere herein.

The method may include grinding up tablets of one or more opioid or opiate agonists into a fine powder of medication. The opioid or opiate agonists that are ground up may include C2 or C3 opiate agonists, tramadol, and/or others. The transdermal cream may include an amount of opioid or opiate agonist of between approximately 1.0% and approximately 5.0% by weight of the transdermal cream. Other amounts may be used, including those discussed elsewhere herein.

The method may include grinding up tablets of one or more NMDA receptor antagonists into a fine powder of medication. The NMDA receptor antagonists that are ground up may be ketamine and/or other antagonists. The transdermal cream may include an amount of NMDA receptor antagonist of between approximately 1.0% and approximately 40.0% by weight of the transdermal cream. Other amounts may be used, including those discussed elsewhere herein.

The method may include grinding up tablets of one or more nerve depressants into a fine powder of medication. The nerve depressants that are ground up may include gabapentin and/or other nerve depressants. The transdermal cream may include an amount of nerve depressant of between approximately 1.0% and approximately 15.0% by weight of the transdermal cream. Other amounts may be used, including those discussed elsewhere herein.

The method may include grinding up tablets of one or more tricyclic antidepressants or other antidepressants into a fine powder of medication. The tricyclic antidepressants that are ground up may include amitriptyline and/or other antidepressants. The transdermal cream may include an amount of antidepressant of between approximately 1.0% and approximately 15.0% by weight of the transdermal cream. Other amounts may be used, including those discussed elsewhere herein.

The fine powder of each active ingredient that is ground up may be added to a transdermal cream or gel separately or collectively. The medications may comprise approximately 20%, approximately 30%, or approximately 40% or more of a transdermal cream by weight. Other amounts may be used, including those discussed elsewhere herein. Alternatively, administering low doses or applying transdermal creams or gels with low concentrations of one or more active ingredients may minimize adverse side effects, such as adverse skin conditions that may develop with usage. Therefore, the method may include adding several medications in fine powder form to a transdermal cream or gel to alleviate the magnitude of any adverse skin conditions that may arise, while simultaneously providing a compounded therapy.

In specific embodiments, the two or more medications that are ground up into a fine powder may include (1) a NSAID (such as meloxicam) and an anticonvulsant (such as lamotrigine and/or topiramate); (2) a NSAID (such as fluribiprofen or nabumetone), a nerve depressant (such as gabapentin), and a muscle relaxant (such as baclofen or cyclobenzaprine); or (3) a NSAID (such as fluribiprofen or nabumetone), a nerve depressant (such as gabapentin), and an antidepressant (such as amitriptyline). Other combinations of medications may be used.

In one aspect, an amount of fine powder of several medications may be ground up and then added to a transdermal cream or gel. The several medications may include: (1) at least one local anesthetic, such as lidocaine and/or prilocaine, in an amount between approximately 1.0% and approximately 7.0% of the transdermal cream by weight; (2) at least one nerve depressant, such as gabapentin, in an amount between approximately 5.0% and approximately 15.0% of the transdermal cream by weight; (3) at least one NSAID, such as flurbiprofen or nabumetone, in an amount between approximately 5.0% and approximately 25.0% of the transdermal cream by weight; and/or (4) at least one muscle relaxant, such cyclobenzaprine, in an amount between approximately 0.5% and approximately 4.0% of the transdermal cream by weight such that multiple ailments may be addressed simultaneously. In one embodiment, the transdermal cream may comprise, by weight of the transdermal cream, approximately 2.0% lidocaine, approximately 2.0% prilocaine, approximately 6.0% gabapentin, approximately 1.0% cyclobenzaprine, and approximately 10.0% flurbiprofen or approximately 20% nabumetone. The several medications may also include an opioid or opiate agonist, a tricyclic or other antidepressant, a NMDA receptor antagonist, and/or other active ingredients.

In another aspect, an amount of fine powder of several medications may be ground up and then added to a transdermal cream or gel. The several medications may include: (1) at least one local anesthetic, such as lidocaine and/or prilocaine, in an amount between approximately 1.0% and approximately 7.0% of the transdermal cream by weight; (2) at least one nerve depressant, such as gabapentin, in an amount between approximately 5.0% and approximately 15.0% of the transdermal cream by weight; (3) at least one NSAID, such as flurbiprofen or nabumetone, in an amount between approximately 5.0% and approximately 25.0% of the transdermal cream by weight; and/or (4) at least one tricyclic antidepressant, such as amitriptyline, in an amount between approximately 0.5% and approximately 4.0% of the transdermal cream by weight. In one embodiment, the transdermal cream may comprise, by weight of the transdermal cream, approximately 2.0% lidocaine, approximately 2.0% prilocaine, approximately 6.0% gabapentin, approximately 1.0% amitriptyline, and approximately 10.0% flurbiprofen or approximately 20.0% nabumetone. The several medications may also include an opioid or opiate agonist, a muscle relaxant, a NMDA receptor antagonist, and/or other active ingredients.

In another aspect, an amount of fine powder of several medications may be ground up and then added to a transdermal cream or gel. The transdermal cream may include lidocaine in an amount between approximately 0.5% and approximately 7.0% by weight of the transdermal cream; prilocaine in an amount between approximately 0.5% and approximately 7.0% by weight of the transdermal cream; meloxicam in an amount between approximately 0.01% and approximately 5.0% by weight of the transdermal cream; and lamotrigine and/or topiramate in an amount between approximately 0.5% and approximately 5.0% by weight of the transdermal cream. In one embodiment, the transdermal cream may comprise approximately 2.0% by weight of both lidocaine and prilocaine, approximately 0.09% by weight meloxicam, and approximately 2.5% by weight lamotrigine and/or topiramate. As a result, the transdermal cream or gel may allow for the topical administration of lidocaine, prilocaine, meloxicam, and lamotrigine and/or topiramate simultaneously during use. The several medications may also include an opioid or opiate agonist, a muscle relaxant, a NMDA receptor antagonist, a nerve depressant, other NSAIDs, other anticonvulsants, and/or other active agents, including those discussed elsewhere herein.

In another aspect, the transdermal cream comprises a nerve depressant, lidocaine, and prilocaine. A fine powder medication of one or more of the above medications may be obtained by crushing tablets of the medication, such as commercial tablets of the nerve depressant. In one such embodiment, the nerve depressant comprises or consists of gabapentin. In a further embodiment, the transdermal cream includes approximately 1% to approximately 10%, approximately 3% to approximately 9%, or approximately 5% to approximately 8% by weight gabapentin and approximately 0.5% to approximately 5.0% by weight of each of lidocaine and prilocaine with DMSO or without DMSO. In one such embodiment, the transdermal cream includes approximately 6% by weight gabapentin and approximately 2% by weight of each of lidocaine and prilocaine. In one embodiment of the above transdermal cream, the transdermal cream includes DMSO. In another embodiment, the transdermal cream does not include DMSO, e.g., DMSO-free.

In a further aspect, the transdermal cream may comprise a nerve depressant, lidocaine, prilocaine, and a NSAID. A fine powder medication of one or more of the above medications may be obtained by crushing tablets of the medication, such as commercial tablets of the nerve depressant and the NSAID. The fine powder medication may also be obtained from bulk sources, which may include powder medication that may be subsequently ground to fine powder or be provided in a fine powder form. In one particular instance of the above embodiment, the nerve depressant comprises or consists of gabapentin and the NSAID comprises or consists of diclofenac. In one embodiment, gabapentin and diclofenac are present in the transdermal cream in an amount approximately 1% to approximately 10%, approximately 1% to approximately 6%, or approximately 2% to approximately 5% by weight gabapentin, approximately 1% to approximately 10%, approximately 2% to approximately 8%, approximately 3% to approximately 7%, or approximately 4% to approximately 6% by weight diclofenac, and approximately 0.5% to approximately 5.0% by weight of each of lidocaine and prilocaine with DMSO or without DMSO. In one such embodiment, the transdermal cream includes approximately 3% by weight gabapentin, approximately 5% by weight diclofenac, and approximately 2% by weight of each of lidocaine and prilocaine. In one embodiment the transdermal cream includes DMSO. In another embodiment the transdermal cream does not include DMSO, e.g., DMSO-free.

In a further aspect, the transdermal cream may comprise a nerve depressant, an NSAID, lidocaine, prilocaine, and a muscle relaxant. A fine powder medication of one or more of the above active ingredients may be obtained by crushing tablets of the medication, such as commercial tablets of the nerve depressant, the NSAID, and the muscle relaxant. The fine powder medication may also be obtained from bulk sources, which may include powder medication that may be subsequently ground to fine powder or be provided in a fine powder form. In one particular instance of the above embodiment, the nerve depressant comprises or consists of gabapentin, the NSAID comprises or consists of diclofenac, and the muscle relaxant comprises cyclobenzaprine. In one embodiment, gabapentin, diclofenac, and cyclobenzaprine are present in the transdermal cream in an amount approximately 1% to approximately 10%, approximately 1% to approximately 6%, or approximately 2% to approximately 5% by weight gabapentin, approximately 1% to approximately 10%, approximately 2% to approximately 8%, approximately 3% to approximately 7%, or approximately 4% to approximately 6% by weight diclofenac, approximately 0.5% to approximately 2%, approximately 0.5% to approximately 1.5% by weight cyclobenzaprine, and approximately 0.5% to approximately 5.0% by weight of each of lidocaine and prilocaine with DMSO or without DMSO. In one such embodiment, the compounded transdermal cream includes approximately 3% by weight gabapentin, approximately 5% by weight diclofenac, approximately 1% by weight cyclobenzaprine, and approximately 2% by weight of each of lidocaine and prilocaine. In one embodiment the compounded transdermal cream includes DMSO. In another embodiment the compounded transdermal cream does not include DMSO, e.g., DMSO-free.

In one aspect, the compounded transdermal cream comprises a NSAID, lidocaine, and prilocaine. A fine powder medication of one or more of the above medications may be obtained by crushing tablets of the medication, such as commercial tablets of the NSAID. In one such embodiment, the NSAID is diclofenac. In a further embodiment, the compounded transdermal cream includes approximately 1% to approximately 10%, approximately 2% to approximately 8%, or approximately 4% to approximately 6% by weight of diclofenac and approximately 0.5% to approximately 5.0% by weight of each of lidocaine and prilocaine with DMSO or without DMSO. In one such embodiment, the compounded transdermal cream includes approximately 5% by weight of diclofenac and approximately 2% by weight of each of lidocaine and prilocaine. In one embodiment of the above transdermal cream, the transdermal cream comprising diclofenac includes DMSO. In another embodiment, the transdermal cream comprising diclofenac does not include DMSO, e.g., DMSO-free.

VIII. Exemplary Embodiments Methods of Compounding Using Solution

In one method of formulating a topically delivered compounded medication, one or more of the active ingredients are provided in an aqueous solution and combined with the base composition comprising lidocaine and prilocaine cream. The lidocaine and prilocaine cream preferably comprises an eutectic mixture of equal quantities (by weight) of lidocaine and prilocaine. The lidocaine and prilocaine cream may thus include an emulsifier. The lidocaine and prilocaine cream may further comprise lidocaine and prilocaine in an emulsion preparation wherein lidocaine and prilocaine are provided at a 1:1 ratio. Preferably the oil phase of the emulsion preparation comprises an eutectic mixture of lidocaine and prilocaine in a ratio of 1:1 by weight. For example, in one embodiment, the lidocaine and prilocaine cream comprises a 5% emulsion preparation, containing 2.5% each of lidocaine and prilocaine. In one embodiment, the lidocaine and prilocaine cream comprises an emulsifier comprising polyoxyethylene fatty acid esters. The lidocaine and prilocaine cream may further comprise a thickening agent. In one embodiment, the thickening agent comprises carboxypolymethylene. The lidocaine and prilocaine cream may further comprise additional excipients or inactive components such as sodium hydroxide and purified water.

In one embodiment, the method of formulating a topically delivered medication in which one or more active ingredients are provided in an aqueous solution and then combined and mixed with the base composition includes combining the aqueous solution and the base composition, wherein lidocaine and prilocaine are already in the cream, such as premixed or pre-incorporated into the cream. For example, the base composition may be a commercially manufactured lidocaine and prilocaine cream, such as lidocaine 2.5% and prilocaine 2.5% cream. In some such embodiments, a suitable lidocaine and prilocaine cream may be a lidocaine and prilocaine cream marketed under the trade name EMLA (Eutectic Mixture of Local Anesthetics) or a generic lidocaine and prilocaine cream, e.g., a lidocaine and prilocaine cream such as those manufactured by Hi-Tech Pharmacal Co., Inc., Amityville, N.Y., or E. Fougera & Co., a division of Fougera Pharmaceuticals Inc., Melville, N.Y. The above commercially manufactured lidocaine and prilocaine creams comprise a 5% emulsion preparation, containing approximately 2.5% of each of lidocaine and prilocaine. The lidocaine and prilocaine cream is provided in an emulsion in which the oil phase is a eutectic mixture of lidocaine and prilocaine, having a ratio of 1:1 by weight, having a melting point below room temperature, and, therefore, both local anesthetics exist as a liquid oil rather than as crystals at room temperature. Each gram of the lidocaine and prilocaine cream may contain lidocaine in an amount approximately 25 mg, prilocaine in an amount approximately 25 mg, polyoxyethylene fatty acid esters (as emulsifiers), carboxypolymethylene or carbomer 934 (as a thickening agent), sodium hydroxide, and purified water to 1 gram.

In various embodiments, the at least one active ingredient in aqueous solution may comprise an NSAID. As described above, the NSAID combined with the base composition may include one or more of: (1) oxicams—meloxicam and piroxicam; (2) salicylic acid derivatives—aspirin, diflunisal, salsalate, and trilisate; (3) propionic acids—flurbiprofen, ibuprofen, ketoprofen, naproxen, and oxaprozin; (4) acetic acids—diclofenac, etodolac, indomethacin, ketorolac, nabumetone, sulindac, and tolmetin; (5) fenamates—meclofenamate; and/or (6) COX-2 inhibitors—celecoxib, rofecoxib, and valdecoxib. In one embodiment, the NSAID comprises a benzeneacetic acid derivative such as diclofenac or pharmaceutically acceptable salt thereof provided in an aqueous solution. For example, the diclofenac may be provided in an aqueous solution comprising a diclofenac sodium solution.

In one embodiment, the diclofenac or pharmaceutically acceptable salt thereof may comprise a diclofenac sodium solution for topical application. The diclofenac sodium solution may contain, for example, 1.5% (w/w) diclofenac sodium wherein each 1 mL of solution may contain approximately 16.05 mg of diclofenac sodium. In one embodiment, the diclofenac solution comprises a diclofenac sodium solution 1.5% (w/w) such as that manufactured under the trade name PENNSAID® by Nuvo Manufacturing, Varennes, Quebec, Canada for treating the pain of osteoarthritis of the knee. The diclofenac solution may also contain various inactive ingredients such as dimethyl sulfoxide USP (DMSO, 45.5% w/w), ethanol, glycerin, propylene glycol and purified water. In one embodiment, the diclofenac solution comprises a diclofenac sodium solution marketed under the trade name PENNSAID® and manufactured by Nuvo Manufacturing, Varennes, Quebec, Canada, in a 2% (w/w) diclofenac solution for treating the pain of osteoarthritis of the knee. Each gram of solution may contain approximately 20 mg of diclofenac sodium and various inactive ingredients such as dimethyl sulfoxide USP (DMSO, 45.5% w/w), ethanol, purified water, propylene glycol, and hydroxypropyl cellulose. In other embodiments, other concentrations of diclofenac solution, such as diclofenac sodium solutions, may be used.

The compounded transdermal cream formulated by combining a commercial NSAID solution such as diclofenac sodium solution with lidocaine and prilocaine cream according to the embodiments described herein possess surprising stability. For example, formulations wherein components comprise a solution and a carboxy polymer cream base often times will "crack". The compounded transdermal cream, however, has been found to be incredibly stable and pristine in appearance. In various embodiments, DMSO makes up approximately 45.5% of the diclofenac solution (1.5% Stock Solution) and comprises approximately 10% of the final finished compound, and the final compound may have approximately 5% DMSO in it.

The combined diclofenac solution and lidocaine and prilocaine cream may be milled, e.g., in an ointment mill, and blended to achieve a desired creamy consistency wherein the active ingredients are approximately evenly dispersed within the compounded transdermal cream.

The compounded transdermal cream formulated by combining a commercially manufactured lidocaine and prilocaine cream and a commercially manufactured diclofenac sodium solution such as a diclofenac sodium may comprise relatively low concentrations of the active ingredients compared to conventional topical formulations including one or more of the active ingredients. Due to the formulation and combination described herein, the present compounded transdermal cream may provide similar effectiveness while having an increased safety profile. The increased safety profile may be especially beneficial to patients with gastric bleeds, on blood thinners, etc. The compounded composition may also provide local anesthetics benefits while promoting deeper penetration into the skin and leveraging DMSO in the diclofenac sodium solution that would be embedded into the compounded transdermal cream.

In a one embodiment, a method of formulating a compounded medication product comprises combining a commercially manufactured lidocaine 2.5% and prilocaine 2.5% cream and a commercially manufactured diclofenac sodium solution such as a diclofenac sodium 1.5% (w/w) or diclofenac sodium 2.0% (w/w) solution to form a compounded transdermal cream whereby the final concentration by weight of the compounded transdermal cream comprises diclofenac or diclofenac sodium at a concentration of approximately 0.1% to approximately 1.0%, lidocaine at a concentration of approximately 1.5% to approximately 2.25%, and prilocaine at a concentration of approximately 1.5% to approximately 2.25%. In further embodiments, the method of formulating a compounded drug product comprises combining a commercially manufactured lidocaine 2.5% and prilocaine 2.5% cream and a commercially manufactured diclofenac solution such as a diclofenac sodium 1.5% (w/w) or diclofenac sodium 2.0% (w/w) solution whereby the final concentration by weight of the compounded drug product comprises diclofenac or diclofenac sodium at a concentration of approximately 0.1% to approximately 0.1% to approximately 0.75%, approximately 0.1% to approximately 0.5%, approximately 0.1% to approximately 0.3%, approximately 0.2% to approximately 0.75%, approximately 0.2% to approximately 0.5%, approximately 0.2% to approximately 0.3%, approximately 0.3% to approximately 0.75%, approximately 0.3% to approximately 0.5%, or approximately 0.5% to approximately 0.75%, lidocaine at a concentration of approximately 1.5% to approximately 2.25%, and prilocaine at a concentration of approximately 1.5% to approximately 2.25%. In further embodiments, the method may also include combining one or more additional active ingredient medications comprising one or more additional NSAIDs, one or more additional local anesthetics, one or more anticonvulsants, one or more nerve depressants, one or more muscle relaxants, one or more antidepressants, one or more NMDA receptor antagonists, or one or more opioid or opiate agonists, and/or other active agents.

The one or more additional NSAIDs that may be further added to or included in the compounded transdermal cream, e.g., combined with the lidocaine and prilocaine cream or the diclofenac sodium solution prior to combining the lidocaine and prilocaine cream and the diclofenac sodium solution or to the compounded transdermal cream comprising the combined diclofenac sodium solution and the lidocaine and prilocaine cream, may be present in an amount between approximately 0.1% and approximately 5.0% by weight of the final compounded transdermal cream and selected from salicylic acid derivatives selected from aspirin, diflunisal, salsalate, and trilisate; propionic acids selected from flurbiprofen, ibuprofen, ketoprofen, naproxen, and oxaprozin; tolmetin; eclofenamate; COX-2 inhibitors selected from celecoxib, rofecoxib, and valdecoxib, oxicams selected from meloxicam, piroxicam; or an additional acetic acid selected from etodolac, indomethacin, ketorolac, nabumetone, and sulindac. The one or more anticonvulsants selected from lamotrigine or topiramate may be added to or included in the compounded transdermal cream, e.g., combined with the lidocaine and prilocaine cream or the diclofenac sodium solution prior to combining the lidocaine and prilocaine cream and the diclofenac sodium solution or to the compounded transdermal cream comprising the combined diclofenac sodium solution and the lidocaine and prilocaine cream, in an amount between approximately 0.1% and approximately 5.0% of the total weight of the final compounded transdermal cream. The one or more nerve depressants may include gabapentin added to or included in the compounded transdermal cream comprising diclofenac, lidocaine, and prilocaine in an amount between approximately 0.1% and approximately 5.0% of the total weight of the final compounded transdermal cream. The one or more muscle relaxants that may be added to or included in the compounded transdermal cream comprising diclofenac, lidocaine, and prilocaine may be provided in an amount between approximately 0.1% and approximately 5.0% of the total weight of the final compounded transdermal cream, wherein the one or more muscle relaxants are selected from baclofen, carisoprodol, chlorzoxazone, cyclobenzaprine, dantrolene, diazepam, metaxalone, methocarbamol, orphenadrine, quinine sulfate, tizanidine, and/or other muscle relaxants. The one or more NMDA receptor antagonists may include ketamine added to or included in the compounded transdermal cream comprising diclofenac, lidocaine, and prilocaine in an amount between approximately 0.1% and approximately 5.0% of the total weight of the final compounded transdermal cream.

In various embodiments, all or a portion of the one or more additional active ingredient medications may comprise a fine powder obtained by grinding commercial tablets of the active ingredient. In some such embodiments or other embodiments, all or a portion of the one or more additional active ingredients may comprise a fine powder obtained from a bulk powder source. The one or more additional active ingredient medications may be dissolved or suspended in a solution or suspension or provided in a solution or suspension and subsequently combined with the lidocaine and prilocaine cream before, after, or along with, e.g., combined with, the diclofenac sodium solution.

In one particular embodiment, one or more additional active ingredients are provided in the form of a fine dry powder obtained from a bulk source, crushed commercial tablets, or both, as described herein, may be dissolved or suspended in a diclofenac sodium 1.5% (w/w) or 2.0% (w/w) solution and then combined with the lidocaine 2.5% and prilocaine 2.5% cream to form the compounded transdermal cream for topical administration. In a one embodiment, one or more additional active ingredients are provided in the form of a fine dry powder obtained from a bulk source, crushed commercial tablets, or both, as described herein, may be combined with the lidocaine and prilocaine 2.5% cream until moistened after which diclofenac sodium 1.5% (w/w) or 2.0% (w/w) solution may be added to form the compounded transdermal cream for topical administration.

A method of compounding the transdermal cream may comprise combining diclofenac sodium solution, fine powder of one or more active ingredient medications obtained from crushed tablets of one or more nerve depressants and/or anticonvulsants, and a lidocaine and prilocaine cream. In one formulation, the one or more anticonvulsants are selected from lamotrigine, topiramate, or a combination thereof and may be added to or included in the compounded transdermal cream, e.g., combined with the lidocaine and prilocaine cream or the diclofenac sodium solution prior to combining the lidocaine and prilocaine cream and the diclofenac sodium solution or to the compounded transdermal cream comprising the diclofenac sodium solution combined with the lidocaine and prilocaine cream, in an amount between approximately 0.1% and approximately 5.0% of the total weight of the final compounded transdermal cream. The one or more nerve depressants may include gabapentin added to or included in the compounded transdermal cream comprising diclofenac, lidocaine, and prilocaine in an amount between approximately 0.1% and approximately 5.0% of the total weight of the final compounded transdermal cream. In one embodiment, diclofenac sodium solution Diclofenac sodium 1.5% (w/w) or diclofenac sodium 2.0% (w/w) solution, the fine powder obtained from crushed tablets of one or more nerve depressants and/or anticonvulsants selected from gabapentin, topiramate, lamotrigine, or combination thereof, and a lidocaine and prilocaine cream, such as a commercially manufactured lidocaine 2.5% and prilocaine 2.5% cream, may be combined to produce the compounded transdermal cream. The fine powder of medication may be combined such that medication introduced from the fine powder is present in the compounded transdermal cream in an amount between approximately 0.1% and 5.0% by weight.

In various embodiments, the diclofenac sodium solution may contain DMSO. For example, DMSO may make up approximately 45.5% of the diclofenac solution (1.5% Stock Solution). The finished compounded transdermal cream may comprise approximately 10% diclofenac sodium 1.5% (w/w) solution and approximately 5% DMSO. Diclofenac sodium 1.5% (w/w) or diclofenac sodium 2.0% (w/w) solution may be added to obtain a concentration by weight of diclofenac or diclofenac sodium in the compounded drug product of approximately 0.05% to approximately 0.25%, approximately 0.05% to approximately 0.2%, approximately 0.05% to approximately 0.15%, approximately 0.1% to approximately 0.15%, approximately 0.12% to approximately 0.15%, or approximately 0.15%. According to one method of making a compounded drug product comprising a transdermal cream having approximately 0.15% diclofenac or diclofenac sodium, approximately 0.1 gm or approximately 0.0935 mL diclofenac sodium 1.5% (w/w) solution may be added per gram of final compounded drug product. The diclofenac sodium solution may be added to the lidocaine and prilocaine cream before, after, or with the fine powder composition. For example, the fine powder may be wetted, dissolved, or suspending in the diclofenac sodium solution and then added to the cream. The diclofenac sodium solution may be added in whole or in part to the cream and the fine powder may be added to the mixture of diclofenac sodium solution and cream. The diclofenac sodium solution may be added in whole or in part to the cream having the fine powder moistened or mixed therein.

The fine powder of medication that includes one or more antidepressants and/or anticonvulsants obtained from ground tablets of medication may include an anticonvulsant in a low amount between approximately 0.1% and approximately 5.0% by weight of the final compounded transdermal cream. In one embodiment, the final compounded transdermal cream comprises approximately 2.5% of lamotrigine, topiramate, or a combination thereof, by weight. Other amounts may be used, including those discussed elsewhere herein. In one embodiment, a fine powder of lamotrigine, topiramate, or combination thereof may be added to a achieve a concentration in the final compounded transdermal cream of approximately 1.0% to approximately 4.0%, approximately 1.0% to approximately 3.0%, approximately 1.0% to approximately 2.5%, approximately 1.5% to approximately 3.0%, approximately 1.5% to approximately 2.5%, approximately 1.5% to approximately 2.5%, or approximately 2.0% to approximately 2.5%. Topiramate tablets for oral administration are produced in various strengths such as 25 mg, 50 mg, 100 mg, and 200 mg strengths. The tablets typically contain additional inactives, which may include candelilla wax, croscarmellose sodium, hypromellose, lactose monohydrate, magnesium stearate, microcrystalline cellulose, macrogol, polyethylene glycol, polysorbate 80, pregelatinised starch, sodium starch glycolate, and titanium dioxide. Colorants may include iron oxides. In one example formulation comprising 2.5% topiramate, each gram of the compounded transdermal cream may include approximately 0.125 tablets of 200 mg topiramate tablets; however, other tablet strengths may be used wherein the amount of topiramate tablet(s) is modified to account for strength difference. The 200 mg topiramate tablets may have an average weight of approximately 0.654 g per tablet. The 200 mg topiramate tablets may be ground to a fine powder. The fine powder may be added in an amount of approximately 0.08175 gm per gram of the final compounded transdermal cream to obtain approximately 25 mg/g or approximately 2.5% topiramate in the final compounded transdermal cream. Lamotrigine tablets for oral administration are produced in various strengths such as 25 mg, 100 mg, 150 mg, and 200 mg strengths. The tablets typically contain additional inactives, which may include colloidal silicon dioxide, lactose monohydrate, magnesium stearate, microcrystalline cellulose, povidone, pregelatinized starch, and sodium starch glycolate. Additional colorants may include FD&C Yellow #6, ferric oxide yellow, and FD&C Blue #2. In one example formulation comprising 2.5% lamotrigine, each gram of the compounded transdermal cream may include approximately 0.125 tablets of 200 mg lamotrigine tablets ground to a fine powder. The amount of fine powder added to obtain approximately 25 mg or 0.025 gm lamotrigine per gram of the final transdermal cream or approximately 2.5% lamotrigine in the final compounded transdermal cream may be determined by multiplying the portion of the tablet providing 25 mg lamotrigine by the weight of the tablet and the final desired weight of the compounded transdermal cream. The proportion of the table providing 25 mg lamotrigine may be determined by dividing 25 mg by the strength of the tablet, 200 mg in this example.

The nerve depressant may be added such that the amount of nerve depressant in the transdermal cream may be between approximately 0.1% and approximately 5.0% of the total weight of the transdermal cream. The nerve depressant may be added in addition to or instead of one or more anticonvulsants. Nerve depressants that may be added may include gabapentin and/or others. Commercially available gabapentin tablets for oral administration include 300 mg, 600 mg, and 800 mg strengths. The tablets typically contain additional inactives, which may include candelilla wax, copolyvidonum, cornstarch, hydroxypropyl cellulose, magnesium stearate, poloxamer 407, and talc. In one embodiment, a fine powder of gabapentin obtained from crushed commercial tablets may be combined with the diclofenac sodium solution and lidocaine and prilocaine cream in an amount sufficient to achieve a concentration of approximately 1.0% to approximately 4.0%, approximately 1.0% to approximately 3.0%, approximately 1.0% to approximately 2.5%, approximately 1.5% to approximately 3.0%, approximately 1.5% to approximately 2.5%, approximately 1.5% to approximately 2.5%, or approximately 2.0% to approximately 2.5% of gabapentin by weight of the final compounded transdermal cream. The gabapentin may be combined with the diclofenac sodium solution and lidocaine and prilocaine cream instead of or in addition to, e.g., in combination with, one or both lamotrigine and topiramate.

The lidocaine and prilocaine cream may be combined in an amount sufficient to provide the final compounded transdermal cream with approximately 1.0% to approximately 5.0%, approximately 1.0% to approximately 4.0%, approximately 1.0% to approximately 3.0%, approximately 1.0% to approximately 2.5%, approximately 1.5% to approximately 3.0%, approximately 1.5% to approximately 2.5%, approximately 1.5% to approximately 2.0%, approximately 1.75% to approximately 2.25%, or approximately 2.0% of each of lidocaine and prilocaine by weight. According to one method of compounding the transdermal cream, the lidocaine and prilocaine cream is a commercially available lidocaine 2.5% and prilocaine 2.5% cream. According to one method of compounded the transdermal cream where the cream comprises approximately 2% of each of lidocaine and prilocaine by weight, 0.8183 gm of lidocaine 2.5% and prilocaine 2.5% cream is added per gram of the final compounded transdermal cream.

An exemplary method of compounding the transdermal cream according to various embodiments described here may comprise grinding tablets comprising the active ingredient medications having nerve depressant activity, such as a nerve depressant, anticonvulsant, or combinations thereof, into a fine powder. A mixing container containing the lidocaine and prilocaine cream may be positioned onto a lift in a powder containment hood and raised into the protected area. Diclofenac sodium solution and the fine powder may be added to the cream in the mixing container. The fine powder may be moistened with the cream to ensure that that dry particles are not dispersed into the surrounding environment during mixing. The mixing container containing the mixture may be transferred to a mixer and mixed for approximately 15 minutes on low. The mixture may then be milled in an ointment mill for approximately an additional 15 minutes on low. The ointment mill may be an Exakt 120S-450 Three Roll Mill, front roller "1", rear roller "3". The compounded transdermal cream may then be packaged in appropriate tubes.

IX. Additional Exemplary Embodiments

The present embodiments may include the presence of DMSO and/or Sterile Water for Irrigation, such as DMSO or Sterile Water for Irrigation in a sufficient quantity to allow for the topical delivery of the active ingredients mentioned herein. For instance, during the methods discussed herein, the DMSO may be removed and replaced with Sterile Water for Irrigation. The transdermal cream may be DMSO-free. The transdermal cream of the present embodiments may be compounded to have no bulk ingredients in it. For example, one or more of the ingredients may be obtained from crushing tablets comprising the ingredients. The tablets may comprise commercially manufactured tablets formulated for oral administration. The tablets may therefore further include various excipients formulated for oral administration, which may include gastrointestinal, sublingual, buccal, or other suitable route of oral administration. According to some embodiments, the transdermal cream of the present embodiments may be compounded with one or more, including, in at least one embodiment, all ingredients obtained through bulk sources. The bulk sources may comprising one or more of the ingredients in a powder, such as a fine powder form.

In one aspect, compounded meloxicam, topiramate (and/or lamotrigine), lidocaine, and prilocaine cream may contain strictly commercially available medications. DMSO, which may be in some cream embodiments disclosed herein, may be replaced with Sterile Water for Irrigation. Sterile Water for Irrigation may act as a primary or sole penetration enhancer in some embodiments.

Although experimentation and investigation continues, it is believed that some detriments may develop from a transition to a DMSO-free compounded transdermal cream. It is believed that the removal of DMSO from certain compounds may decrease the effectiveness of the compound given that the primary penetrant is no longer present. Also, patients that have received the previous compounded version containing DMSO may experience lower efficacy rates. It is also believed that the transition of the formula may, at best, give the same efficacy that the patients previously had experienced, and, at worst, decrease efficacy due to the absence of DMSO.

On the other hand, the use of Sterile Water for Irrigation instead of DMSO may be cheaper and involve an easier method of manufacture. Also, Sterile Water for Irrigation is an FDA-approved commercially available medication.

In one embodiment, the transdermal cream comprises a nerve depressant, lidocaine, and prilocaine. A method of compounding the transdermal cream may comprise adding the fine powder medication comprising the nerve depressant to a starting transdermal cream or base. As described above, the fine powder medication may be obtained by crushing tablets of the medication, such as commercial tablets of the nerve depressant. As also described above, the fine powder medication may be obtained using bulk sources, which may include powder that may be ground to fine powder or the medication in a fine powder form. The fine powder of medication, e.g., nerve depressant, may be added to a transdermal cream or base composition containing both lidocaine and prilocaine. In another embodiment, the fine powder medication added to the transdermal cream or base composition further includes one or both lidocaine and prilocaine. In one particular instance of the above embodiment, the nerve depressant comprises or consists of gabapentin. In a further embodiment, gabapentin is added to the starting transdermal cream or base composition in a sufficient amount such that the final transdermal cream includes the approximately 1% to approximately 10%, approximately 3% to approximately 9%, or approximately 5% to approximately 8% by weight gabapentin and approximately 0.5% to approximately 5.0% by weight of each of lidocaine and prilocaine with DMSO or without DMSO. In one such embodiment gabapentin is added to the starting transdermal cream or base composition in a sufficient amount such that the final transdermal cream includes the approximately 6% by weight gabapentin and approximately 2% by weight of each of lidocaine and prilocaine. In one embodiment the final transdermal cream includes DMSO. In another embodiment the final transdermal cream does not include DMSO. For example, the method of compounding the above transdermal cream may include addition of DMSO to the starting transdermal cream or base or to the cream or base after gabapentin has been added or at an intermediate point of the compounding process. As described herein, all or a portion of the fine powder medication may be wetted with DMSO prior to addition to the transdermal cream. In embodiments without DMSO, the fine powder medication may be added directly to the cream or base or, in some embodiments, the fine powder medication may be wetted with liquid such as Sterile Water for Irrigation.

In a further embodiment, the transdermal cream comprises a nerve depressant, lidocaine, prilocaine, and a NSAID. The method of compounding the transdermal cream may further comprise adding the fine powder medication comprising the nerve depressant and NSAID to a starting transdermal cream or base. The fine powder medication comprising the fine powders of the nerve depressant and NSAID may be added together or separate. As described above, the fine powder medication may be obtained by crushing tablets of the medication, such as commercial tablets of the nerve depressant and the NSAID. As also described above, the fine powder medication may be obtained from bulk sources, which may include powder medication that may be ground to fine powder or the medication in a fine powder form. The fine powder medication, e.g., a nerve depressant and NSAID, may be added to the transdermal cream or base composition containing both lidocaine and prilocaine, which may be a commercially manufactured lidocaine and prilocaine cream, such as lidocaine 2.5% and prilocaine 2.5% cream. In another embodiment, the fine powder medication added to the transdermal cream or base composition further includes one or both lidocaine and prilocaine. In one particular instance of the above embodiment, the nerve depressant comprises or consists of gabapentin and the NSAID comprises or consists of diclofenac. In one embodiment, gabapentin and diclofenac are added to the starting transdermal cream or base composition in a sufficient amount such that the final transdermal cream includes approximately 1% to approximately 10%, approximately 1% to approximately 6%, or approximately 2% to approximately 5% by weight gabapentin, approximately 1% to approximately 10%, approximately 2% to approximately 8%, approximately 3% to approximately 7%, or approximately 4% to approximately 6% by weight diclofenac, and approximately 0.5% to approximately 5.0% by weight of each of lidocaine and prilocaine with DMSO or without DMSO. In one such embodiment gabapentin and diclofenac are added to the starting transdermal cream or base composition in sufficient amounts such that the final transdermal cream includes the approximately 3% by weight gabapentin, approximately 5% by weight diclofenac, and approximately 2% by weight of each of lidocaine and prilocaine. In one embodiment the final transdermal cream includes DMSO. In another embodiment the final transdermal cream does not include DMSO. For example, the method of compounding the above transdermal cream may include addition of DMSO to the starting transdermal cream or base or to the cream or base after gabapentin, diclofenac, or both have been added or at an intermediate point of the compounding process. As described herein, all or a portion of the fine powder medication may be wetted with DMSO prior to addition to the starting transdermal cream or base composition. In embodiments without DMSO, the fine powder medication may be added directly to the cream or base or, in some embodiments, the fine powder medication may be wetted with liquid such as Sterile Water for Irrigation.

In additional embodiments, the compounded transdermal cream comprises a nerve depressant, NSAID, lidocaine, prilocaine, and a muscle relaxant. The method of compounding the transdermal cream may further comprise adding the fine powder medication comprising the nerve depressant, NSAID, and muscle relaxant to a starting transdermal cream or base. The fine powder medication comprising the fine powders of the nerve depressant, NSAID, and muscle relaxant may be added together or separate. As described above, the fine powder medication may be obtained by crushing tablets of the medication, such as commercial tablets of the nerve depressant, the NSAID, the muscle relaxant. As also described above, the fine powder medication may be obtained from bulk sources, which may include powder medication that may be ground to fine powder or the medication in a fine powder form. The fine powder medication, e.g., the nerve depressant, the NSAID, and the muscle relaxant, may be added to the transdermal cream or base composition containing both lidocaine and prilocaine. In another embodiment, the fine powder medication added to the transdermal cream or base composition further includes one or both lidocaine and prilocaine, which may be a commercially manufactured lidocaine and prilocaine cream, such as lidocaine 2.5% and prilocaine 2.5% cream. In one particular form of the above embodiment, the nerve depressant comprises or consists of gabapentin, the NSAID comprises or consists of diclofenac, and the muscle relaxant comprises or consists of cyclobenzaprine. In one embodiment, gabapentin, diclofenac, and cyclobenzaprine are added to the starting transdermal cream or base composition in a sufficient amount such that the final transdermal cream includes the approximately 1% to approximately 10%, approximately 1% to approximately 6%, or approximately 2% to approximately 5% by weight gabapentin, approximately 1% to approximately 10%, approximately 2% to approximately 8%, approximately 3% to approximately 7%, or approximately 4% to approximately 6% by weight diclofenac, approximately 0.5% to approximately 1.5% by weight cyclobenzaprine and approximately 0.5% to approximately 5.0% by weight of each of lidocaine and prilocaine with DMSO or without DMSO. In one such embodiment gabapentin and diclofenac are added to the starting transdermal cream or base composition in sufficient amounts such that the final transdermal cream includes the approximately 3% by weight gabapentin, approximately 5% by weight diclofenac, approximately 1% by weight cyclobenzaprine, and approximately 2% by weight of each of lidocaine and prilocaine. In one embodiment the final transdermal cream includes DMSO. In another embodiment the final transdermal cream does not include DMSO. For example, the method of compounding the above transdermal cream may include addition of DMSO to the starting transdermal cream or base or to the cream or base after gabapentin, diclofenac, or both have been added or at an intermediate point of the compounding process. As described herein, all or a portion of the fine powder medication may be wetted with DMSO prior to addition to the starting transdermal cream or base composition. In embodiments without DMSO, the fine powder medication may be added directly to the cream or base or, in some embodiments, the fine powder medication may be wetted with liquid such as Sterile Water for Irrigation.

In one embodiment, the transdermal cream comprises a NSAID, lidocaine, and prilocaine. A method of compounding the transdermal cream may comprise adding the fine powder medication comprising the NSAID to a starting transdermal cream or base. As described above, the fine powder medication may be obtained by crushing tablets of the medication, such as commercial tablets of the NSAID. As also described above, the fine powder medication may be obtained using bulk sources, which may include powder that may be ground to fine powder or the medication in a fine powder form. The fine powder of medication, e.g., NSAID, may be added to a transdermal cream or base composition containing both lidocaine and prilocaine, which may be a commercially manufactured lidocaine and prilocaine cream, such as lidocaine 2.5% and prilocaine 2.5% cream. In another embodiment, the fine powder medication added to the transdermal cream or base composition further includes only one lidocaine and prilocaine. In one particular instance of the above embodiment, the NSAID comprises or consists of diclofenac. In a further embodiment, diclofenac is added to the starting transdermal cream or base composition in a sufficient amount such that the final transdermal cream includes the approximately 1% to approximately 10%, approximately 2% to approximately 8%, or approximately 4% to approximately 6% by weight of diclofenac and approximately 0.5% to approximately 5.0% by weight of each of lidocaine and prilocaine with DMSO or without DMSO. In one such embodiment either the diclofenac or the ibuprofen is added to the starting transdermal cream or base composition in a sufficient amount such that the final compounded transdermal cream includes the approximately 5% by weight diclofenac and approximately 2% by weight of each of lidocaine and prilocaine. In one embodiment the final compounded transdermal cream includes approximately 5% by weight diclofenac and DMSO. In another embodiment the final compounded transdermal cream does not include DMSO. For example, the method of compounding the above transdermal cream may include addition of DMSO to the starting transdermal cream or base or to the cream or base after diclofenac has been added or at an intermediate point of the compounding process. As described herein, all or a portion of the fine powder medication, for example, the diclofenac, may be wetted with DMSO prior to addition to the transdermal cream. In embodiments without DMSO, the fine powder medication, for example, the ibuprofen, may be added directly to the cream or base or, in some embodiments, the fine powder medication, for example, the ibuprofen, may be wetted with liquid such as Sterile Water for Irrigation.

In one aspect, a transdermal cream that permits the simultaneous administration of multiple medications in low concentrations may be provided. The transdermal cream may include lidocaine in an amount between approximately 0.5% and approximately 7.0% by weight of the transdermal cream; prilocaine in an amount between approximately 0.5% and approximately 7.0% by weight of the transdermal cream; meloxicam in an amount between approximately 0.01% and approximately 5.0% by weight of the transdermal cream; and lamotrigine in an amount between approximately 0.5% and approximately 5.0% by weight of the transdermal cream. In one embodiment, the transdermal cream may comprise approximately 2.0% by weight of both lidocaine and prilocaine, approximately 0.09% by weight meloxicam, and approximately 2.5% by weight lamotrigine. As a result, the transdermal cream may allow for the topical administration of lidocaine, prilocaine, meloxicam, and lamotrigine simultaneously during use. The transdermal cream may further include only or primarily Sterile Water for Irrigation as a penetration enhancer or other component, and be devoid of DMSO or DMSO-free.

In another aspect, a transdermal cream that permits the simultaneous administration of multiple medications in low concentrations may be provided. The transdermal cream may include lidocaine in an amount between approximately 0.5% and approximately 7.0% by weight of the transdermal cream; prilocaine in an amount between approximately 0.5% and approximately 7.0% by weight of the transdermal cream; meloxicam in an amount between approximately 0.01% and approximately 5.0% by weight of the transdermal cream; and topiramate in an amount between approximately 0.5% and approximately 5.0% by weight of the transdermal cream. In one embodiment, the transdermal cream may comprise approximately 2.0% by weight of both lidocaine and prilocaine, approximately 0.09% by weight meloxicam, and approximately 2.5% by weight topiramate. As a result, the transdermal cream may allow for the topical administration of lidocaine, prilocaine, meloxicam, and topiramate simultaneously during use. The transdermal cream may further include only or primarily Sterile Water for Irrigation for penetration enhancement or as a wetting component, and/or be devoid of DMSO or DMSO-free.

In another aspect, a method of compounding one or more medications with a transdermal cream for the topical administration of a compounded therapy may be provided. The method may include grinding up one or more tablets of a NSAID, an anticonvulsant, a nerve depressant, a muscle relaxant, a NMDA (N-Methyl-D-aspartate) receptor antagonist, an opiate or opioid agonist, and/or antidepressant into a fine powder of medication. In an alternate aspect, one or more, including all, of the medications may be obtained from bulk sources. The medications obtained from bulk sources may be in the form of a powder, which may be a fine powder or may be further ground into a fine powder prior to compounding with the transdermal cream or gel, which may be a commercially manufactured lidocaine and prilocaine cream, such as lidocaine 2.5% and prilocaine 2.5% cream. The method may include wetting the fine powder of medication mixture with DMSO or Sterile Water for Irrigation. The method may also include adding the fine powder of medication to a transdermal cream or base composition containing both lidocaine and prilocaine, the transdermal cream including both lidocaine and prilocaine in an amount of between approximately 0.5% and approximately 7.0% by weight of the transdermal cream, respectively. The method may include adding the fine powder of compounded medication to the starting transdermal cream or base composition in a sufficient amount such that the final transdermal cream includes the compounded medication that is ground up in a low amount of between approximately 0.01% and approximately 5.0% by weight of the transdermal cream. In one embodiment, an amount of ground up medication is added to the base composition such that the final transdermal cream contains low concentrations of several active ingredients and is approximately 2.0% by weight lidocaine, approximately 2.0% by weight prilocaine, approximately 0.09% by weight meloxicam, and approximately 2.5% by weight either lamotrigine or topiramate. In one embodiment, the transdermal cream may further include only or primarily Sterile Water for Irrigation for penetration enhancement or as a wetting component, and/or be devoid of DMSO or DMSO-free.

In another aspect, a method of compounding medications with a transdermal cream for the topical administration of a compounded therapy may be provided. The method may include grinding up tablets of two or more medications into a fine powder of compounded medication. The two or more compounded medications to be ground up may be selected from a NSAID, an anticonvulsant, a nerve depressant, a muscle relaxant, a NMDA receptor antagonist, a local anesthetic, an antidepressant, and an opioid or opiate agonist. The method may include wetting the fine powder of compounded medication with DMSO or Sterile Water for Irrigation. The method may include then adding the fine powder of compounded medication to a transdermal cream or gel such that the transdermal cream or gel allows for topical delivery of the two or more compounded medications for simultaneous treatment of two or more ailments when the transdermal cream or gel is topically applied. The transdermal cream may further include only or primarily Sterile Water for Irrigation for penetration enhancement or as a wetting component, and/or be devoid of DMSO or other penetration enhancers.

The present invention may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

What is claimed is:

1. A method of producing a compounded medication, the method comprising:
    formulating a compounded transdermal cream comprising combining a first component and a second component, and mixing the combined first component and second component;
    wherein the first component comprises a diclofenac sodium solution comprising diclofenac, DMSO, propylene glycol, purified water, and at least one of glycerin or hydroxypropyl cellulose,
    wherein the second component comprises a lidocaine 2.5% and prilocaine 2.5% cream comprising a eutectic mixture of lidocaine 2.5% and prilocaine 2.5% and polyoxyethylene fatty acid esters, sodium hydroxide, purified water, and at least one of carboxypolymethylene or carbomer 934, and
    wherein the first component and the second component are combined in amounts such that the compounded transdermal cream comprises diclofenac in an amount between 0.1% and 0.75% by weight of the compounded transdermal cream and lidocaine 2.5% and prilocaine 2.5% cream in an amount between 60% and 90% by weight of the compounded transdermal cream, and wherein the percent weights of lidocaine and prilocaine are in matched amounts.

2. The method of claim 1, wherein the diclofenac sodium solution is a commercially manufactured diclofenac sodium 1.5% (w/w) solution.

3. The method of claim 2, wherein the first component and the second component are combined in amounts such that the compounded transdermal cream comprises between 0.1% and 0.5% diclofenac by weight of the compounded transdermal cream.

4. The method of claim 2, wherein first component and the second component are combined in amounts such that the compounded transdermal cream comprises between 0.3% and 0.75% diclofenac by weight of the compounded transdermal cream.

5. The method of claim 2, further comprising combining a third component with the first component and the second component, wherein the third component is a fine powder of additional medication obtained from crushed tablets of one or more nerve depressants, anticonvulsants, or combinations thereof, and wherein the fine powder is combined with the first component and the second component in an amount such that the compounded transdermal cream comprises the additional medication in an amount between 1.0% and 5.0% by weight.

6. The method of claim 5, wherein the additional medication is selected from the group consisting of lamotrigine, topiramate, gabapentin, or combination thereof.

7. The method of claim 6, wherein first component is combined in an amount such that the compounded transdermal cream comprises 0.15% by weight diclofenac, wherein the second component is combined in an amount such that the compounded transdermal cream comprises 80% by weight lidocaine 2.5% and lidocaine 2.5% cream by weight, and wherein the third component is combined in an amount such that the compounded transdermal cream comprises 2.5% by weight of the additional medication.

8. The method of claim 1, wherein the compounded medication is devoid of gabapentin.

* * * * *